US011427831B2

(12) United States Patent
Immanen et al.

(10) Patent No.: US 11,427,831 B2
(45) Date of Patent: Aug. 30, 2022

(54) METHOD FOR IMPROVING STEM VOLUME GROWTH AND BIOMASS PRODUCTION IN TREES

(71) Applicant: STORA ENSO OYJ, Helsinki (FI)

(72) Inventors: Juha Immanen, Helsinki (FI); Yrjö Helariutta, Helsinki (FI); Kaisa Nieminen, Helsinki (FI)

(73) Assignee: Stora Enso OYJ, Helsinki (FI)

( * ) Notice: Subject to any disclaimer, the term of this patent is extended or adjusted under 35 U.S.C. 154(b) by 579 days.

(21) Appl. No.: 16/200,012

(22) Filed: Nov. 26, 2018

(65) Prior Publication Data

US 2019/0185872 A1 Jun. 20, 2019

Related U.S. Application Data

(63) Continuation of application No. 15/108,992, filed as application No. PCT/FI2014/051057 on Dec. 29, 2014, now abandoned.

(30) Foreign Application Priority Data

Dec. 30, 2013 (FI) ..................................... 20136335

(51) Int. Cl.
C12N 15/82 (2006.01)
C12N 9/10 (2006.01)

(52) U.S. Cl.
CPC ....... *C12N 15/8261* (2013.01); *C12N 9/1085* (2013.01); *C12N 15/8229* (2013.01); *C12N 15/8295* (2013.01); *C12Y 205/01027* (2013.01); *C12N 9/10* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 7,345,216 | B2 | 3/2008 | Keetman et al. |
| 2005/0183159 | A1 | 8/2005 | Clark et al. |
| 2006/0064786 | A1 | 3/2006 | Brugiere |
| 2007/0180580 | A1 | 8/2007 | Hertzberg |

FOREIGN PATENT DOCUMENTS

| | | |
|---|---|---|
| EP | 1033405 A2 | 9/2000 |
| EP | 1384776 A1 | 1/2004 |
| EP | 1522586 A1 | 4/2005 |
| EP | 1384776 B1 | 9/2009 |
| JP | 2007197355 A | 9/2007 |
| WO | 0210210 A2 | 2/2002 |
| WO | 2004074442 A2 | 9/2004 |
| WO | 2004097024 A1 | 11/2004 |
| WO | 2006034286 A2 | 3/2006 |
| WO | 2007090143 A2 | 8/2007 |

OTHER PUBLICATIONS

Shahmuradov et al. Nucleic Acids Research, 2017, vol. 45, No. 8, 1-12. (Year: 2017).*
Nieminen et al. Proceedings of the National Academy of Sciences 105.50 (2008): 20032-20037. (Year: 2008).*
UniProt Accession Q94ID1, entered Feb. 9, 2010. (Year: 2010).*
Genbank Accession No. EU583454, dated Dec. 31, 2008. (Year: 2008).*
Matsumoto-Kitano et al. Proceedings of the National Academy of Sciences 105.50 (2008): 20027-20031. (Year: 2008).*
Zuo, et al. (The Plant Journal 24.2 (2000): 265-273). (Year: 2000).*
RN: 878821-76-2. PN: US20060064786 SEQID: 37 unclaimed protein.
RN: 849382-58-7. PN: EP1522586 SEQID: 17 unclaimed DNA.
RN: 742225-86-1 Protein (*Arabidopsis thaliana* clone WO2004074442-SEQID-35).
RN: 302660-97-5, EP1033405A2 DNA (*Arabidopsis thaliana* clone Ceres_2153076 fragment).
RN: 395137-18-5 Herbicide-target protein (*Arabidopsis thaliana* clone WO0210210-SEQID-1616).
RN: 340063-16-3. PN US20050183159A1, (*Arabidopsis thaliana* strain Wassilewskija gene AtIPT7 cDNA plus flanks).
RN:849381-46-0 and RN: 282742-36-3 contained in attached transcript.
EMBL-EBI: AC. Q94ID1, Version 71, published on Jul. 24, 2013.
International Searching Authority, International Search Report and Written Opinion, PCT/FI2014/051057, dated Apr. 1, 2015.
Search Report issued by the Finish Patent and Registration office for Patent Application No. 20136335, dated Sep. 18, 2014.
Matsumoto-Kitano, M., et. al. "Cytokinins are central regulators of cambial activity", 2008, In: PNAS, vol. 105, pp. 20027-20031.
Elo. A., et. al. "Stem cell function during plant vascular development", 2009, In: Seminars in Cell & Developmental Biology, vol. 20, pp. 1097-1106.
Nieminen, K., et. al. "Cytokinin signaling regulates cambial development in poplar", 2008, In: PNAS, vol. 105, pp. 20032-20037.
Dello, Ioio R., et. al. "A PHABULOSA/Cytokinin Feedback Loop Controls Root Growth in *Arabidopsis*", 2012, In: Current Biology, vol. 22, pp. 1699-1704.
Von Schwartzenberg, K., et. al. "Enhancement of the endogenous cytokinin concentration in poplar by transformation with Agrobacterium T-DNA gene ipt. Tree Physiology", Jan. 1994, vol. 14, No. 1, pp. 27-35.

(Continued)

Primary Examiner — Charles Logsdon
(74) Attorney, Agent, or Firm — Greer, Burns, Crain, Ltd.

(57) ABSTRACT

The present invention relates to a genetic construct comprising a nucleic acid sequence encoding cytokinin biosynthetic isopentenyl-transferase enzyme (IPT) operable linked to a promoter allowing expression of said nucleic acid sequence in cambial cells. The invention relates also a method for producing a transgenic plant capable of increased biomass production and/or increased stem volume growth compared to wild type plant and a method for improving the production of biomass and/or increased stem volume growth in trees, as well as to a tree that over expresses an endogenous or exogenous nucleic acid sequence encoding IPT in cambial cells and a wood product obtainable from the transgenic tree.

17 Claims, 5 Drawing Sheets

Specification includes a Sequence Listing.

(56) References Cited

OTHER PUBLICATIONS

Botti, S., et. al. "Production of ipt-expressing white poplar lines (*Populus alba* L.) with abnormal root morphology", Caryologia, 2007, vol. 60, No. 1-2, pp. 175-177.
Honda, C. et. al. "Transformation of kiwifruit using the ipt gene alters tree architecture.", Plant Cell, Tissue and Organ Culture (PCTOC), Oct. 2011, vol. 107, No. 1, pp. 45-53.
Strabala, T. J., et. al. "Levels and location of expression of the Agrobacterium tumefaciens ppTiA6 ipt gene promoter in transgenic tobacco", Plant Molecular Biology, Mar. 2003, vol. 21, No. 6, pp. 1011-1021.
Van Beveren, K. S., et. al. "Transformation of cambial tissue in vivo provides an efficient means for induced somatic sector analysis and gene testing in stems of woody plant species", Functional Plant Biology, 2006, vol. 33, No. 7, pp. 629-638.
Dai, W., et. al. "Expression of β-glucuronidase Gene in Aspen under Control of CaMV35S, Heat Shock and RoIC Promoters", Hortscience, Jun. 2000, vol. 35, No. 3, p. 478.
Supplemental European Search Report and Opinion for corresponding European Application No. EP14876044, dated Apr. 26, 2017.
Young Im Choi et al., Low Level Expression of Prokaryotic TZS Gene Enhances Growth Performance of Transgenic Poplars, TREES: Structure and Function, pp. 741-750, Mar. 10, 2009, vol. 23, No. 4, Springer, Berlin, DE.
Robertas Ursache et al., Genetic and Hormonal Regulation of Cambial Development, Physiologia Plantarum, pp. 36-45, Jan. 3, 2013, vol. 147, No. 1.
Miyawaki, Kaori, et al., Expression of cytokinin biosynthetice isopentenyltransferase genes in *Arabidopsis*: tissue specificity and regulation by auxin, cytokinin, and nitrate, The Plant Journal, 2004, 37, 128-138.
Zhang, Jing, et al., *Arabidopsis* as a model for wood formation, Science Direct, Current Opinion in Biology 2011, 22:293-299.
Guo, Haiwei H., et al., Protein Tolerance to Random Amino Acid Change, PNAS, 2004, vol. 101, No. 25, 9205-9210.
Shahmuradov, Iiham A., TSSPlant: a new tool for prediction of plant Pol II promoters, Nucleic Acid Research, 2017, vol. 45, No. 8.

UniProt Accession Q941D1, entered Feb. 9, 2010.
Genbank Accession No. EU583454, entered Dec. 31, 2008.
Walden, Richard, et al., The Use of Gene Vectors in Plant Molecular Biology, Methods in Molecular and Cellular Biology, vol. 1, No. 516, 1990, pp. 175-194.
Tuskan, G.A., et al., The Genome of Black Cottonwood, Poplular Trichocarpa (Torr. & Gray), Science, vol. 313, 2006, p. 1596-1604.
Seppanen, S.K., et al., Antifungal Activity of Stilbenes in in Vitro Bioassays and in Transgenic Populus Expressing a Gene Encoding Pinosylvin Synthase, Plant Cell Rep. (2004), 22:584-593.
Ei-Showk, Sedeer, et al., Crossing Paths: Cytokinin Signalling and Crosstalk, Development 140, 1373-1382 (2013), Finland.
Haggman, Hely, et al., Expression of Vitreoscilla Haemoglobin in Hybrid Aspen (Populus Tremula x Tremuloides), Plant Biotechnology Journal (2003) 1, 287-300.
Love, Jonathan, et al, Ethylene is an Endogenous Stimulator of Cell Division in the Cambial Meristem of Populus, PNAS, vol. 106, No. 14, 5984-5989, 2009.
Sakakibara, Hitoshi, Cytokinins: Activity, Biosynthesis and Translocation, Annu. Rev. Plant Biol. 2006.57:431-449.
Kakimoto, Tatsuo, Identification of Plant Cytokinin Biosynthetic Enzymes as Dimethylallyl Diphosphate: ATP/ADP Isopentenyltransferases, Plant Cell Physiol, 42 (7): 677-685 (2001).
Nillson, Ove, et al., Spatial Pattern of Cauliflower Mosaic Virus 35S Promoter-Luciferase Expression in Transgenic Hybrid Aspen Trees Monitored by Enzymatic Assay and Non-Destructive Imaging, Transgenic Research 1, 209-220 (1992).
Altschul, Stephen F., et al., Basic Local Alignment Search Tool, J. Mol. Biol (1990), 215, 403-410.
Koncz, Csaba, et al., Specialized Vectors for Gene Tagging and Expression Studies, Plant Molecular Biology Manual, B2, 1-22, 1994.
Skoog, Folke, et al., Chemical Regulation of Growth and Organ Formation in Plant Tissues Cultured In Vitro, Department of Botany, University of Wisconsin, Symp Soc Exp Biol, 1957, 11:118-130.
Non Final Office Action from U.S. Appl. No. 15/108,992, dated Dec. 1, 2017.
Final Office action from U.S. Appl. No. 15/108,992 dated Jul. 24, 2018.

\* cited by examiner domain A          GxTxxGK[ST] (SEQ ID NO:3)

domain B          [VLI]xxxxxxx[VLI][VLI]xxDxxQ (SEQ ID NO:4)

domain C          [VLI][VLI]xGG[ST] (SEQ ID NO:5)

Fig.2

METHOD FOR IMPROVING STEM VOLUME GROWTH AND BIOMASS PRODUCTION IN TREES

This application is a U.S. Continuation Application of U.S. application Ser. No. 15/108,992, filed Jun. 29, 2016, which is a U.S. National Stage under 35 U.S.C. § 371 of International Application No. PCT/FI2014/051057, filed Dec. 29, 2014, which claims priority to Finnish application No. 20136335 filed Dec. 30, 2013.

FIELD OF THE INVENTION

The present invention relates to a method for producing a transgenic plant capable of increased stem volume growth and/or biomass production and also to a method for improving the stem volume growth and/or the production of biomass in trees. The invention relates also to a genetically modified tree, a wood product derived from said tree, genetic constructs and vectors and a tree expressing said genetic constructs and vectors.

BACKGROUND OF THE INVENTION

Activity of vascular cambium, the lateral meristem of woody plant species, gives rise to the secondary vascular tissues. Cambial meristem forms a thin cylinder along a tree trunk (or a root or branch), and it produces new vascular tissues both inwards and outwards. These tissues, secondary xylem and phloem, form the bulk of lateral growth in plant organs. The conducting vascular cells in both of them acquire their final functional form gradually, through a multi-step differentiation process. The developing xylem cells will undergo expansion, secondary cell wall formation, programmed cell death and final lignification. Similarly, functional phloem cells will be formed through the succession of several developmental steps, including the differentiation of sieve elements and companion cells. These multi-step differentiation programs form two oppositely oriented developmental gradients across the cambial region; the further apart a phloem or xylem cell is from the meristematic middle, the more advanced it is in its differentiation process. Remarkably, the core of cambial meristem; the actively dividing cells, retain their meristematic nature and remain undifferentiated into either form of vascular tissues. Periclinal cell divisions both renew the population of meristematic cells and provide nascent material for vascular tissue differentiation programs, whereas anticlinal divisions enable the creation of novel cell files and expansion of the cambial circle.

The scale of secondary development is highly different in tree species; they display an extreme and economically highly valuable capacity for wood production during their long lifespan. Potentially as an adaptation for the massive secondary growth, the wood of most trees also contains an extensive lateral transport system, the vascular ray network. Other novel challenges for the cambial function of perennial tree species are presented by the annual activity-dormancy cycle. To ensure their survival, trees must adapt their cambial activity to the yearly cycle of cold and warm (or wet and dry) seasons. They must be able to activate their cambial meristem in the spring and deactivate it into a dormant resting stage during the autumn.

It would be highly valuable for the economy of wood production, if the growth of trees could be improved and if, in particular, the stem volume could be enhanced.

Cytokinin signaling has been shown to be required for cambial function. Transgenic *Populus* trees with impaired cytokinin signaling displayed compromised radial growth caused by a decreased number of cell divisions in the vascular cambium (Nieminen et al., 2008). In addition, genes encoding cytokinin receptors and cytokinin primary response genes were abundant in the cambial region of *Populus* stem (Nieminen et al., 2008).

Although it is known that cytokinin signaling is connected to tree biomass production, the picture is complicated, since there are at least some 100 cambium enriched and cytokinin regulated genes with several functions. It is not known which of these genes are needed for radial growth of stem cells (Tuskan et al., 2006).

To add further complexity the hormonal regulation of cambium, studies in other tissues have revealed a highly interconnected network between cytokinin and auxin signaling (El-Showk et al., 2013). Cytokinin can affect both auxin biosynthesis and transport. Interestingly, this regulation appears to be highly complex, as there have been several reports about both positive and negative effects of cytokinin on auxin biosynthesis. Similar results have been obtained about the effect of cytokinin on auxin transport, where this hormone has been reported to both up- and downregulate auxin transporter levels. Most probably these diverse results reflect fine-tuned regulation patterns; cytokinin may have different effect on different auxin biosynthetic enzymes and transporters, most probably on a tissue-specific manner. On top of that, also auxin is known to have a similarly complex role in the regulation of cytokinin biosynthesis and signaling.

International patent publication WO 2006/034286 describes compositions and methods which employ isopentenyl transferase (IPT) polypeptides and polynucleotides that are involved in modulating plant development. In the methods described expression of the IPT maintains or improves for example the stress tolerance of the plant, maintains or increases the size of the plant, maintains seed set, or increases shoot growth.

Although some attempts have been made in the prior art to improve plant growth, there is still a need for methods and constructs which could be used to improve tree growth, in particular to improve stem volume growth and biomass production.

SUMMARY OF THE INVENTION

One object of the present invention is to provide a solution to the problems encountered in the prior art. Specifically, the present invention aims to provide a solution how to improve the growth of trees. Furthermore, the present invention aims to increase the stem volume growth and production of biomass in trees.

In particular, it is one object of the present invention to provide a solution, which improves radial growth in trees. To achieve these objects the invention is characterized by the features that are enlisted in the independent claims. Other claims represent the preferred embodiments of the invention.

The invention is based on the finding that it is possible to enhance the cell division in the cambial cells by enhancing the cytokine signaling in cambial cells. More specifically, it is possible to enhance the cell division in cambial cells by allowing expression of specific genes encoding cytokinin biosynthetic isopentenyl-transferase enzyme in cambial cells.

It has now been surprisingly found that by enhanced expression of cytokinin biosynthetic isopentenyl-transferase enzyme in cambial cells results in enhanced stem volume growth and/or increased biomass production.

Hence, in one aspect, the present invention provides a genetic construct comprising a first nucleic acid sequence (effector) encoding cytokinin biosynthetic isopentenyl-transferase enzyme operable linked to a second nucleic acid sequence (promoter) allowing expression of said first nucleic acid sequence in cambial cells as defined in claim 1.

The present invention provides in another aspect a vector comprising the genetic construct as defined in claim 7.

Hence, in a third aspect, the present invention provides a tree which overexpresses an endogenous nucleic acid sequence, or expresses an exogenous nucleic acid sequence, encoding cytokinin biosynthetic isopentenyl-transferase enzyme in cambial cells as defined in claim 8.

In a fourth aspect, the present invention provides a wood product obtainable from the tree as defined in claim 16.

In a fifth aspect, the present invention provides a method for producing a transgenic plant capable of increased biomass production and/or increased stem volume growth compared to wild type plant as defined in claim 17.

In a sixth aspect, the present invention provides a method for improving the production of biomass and/or increased stem volume growth in trees as defined in claim 18.

BRIEF DESCRIPTION OF THE FIGURES

FIG. 2. Conserved domains within IPTs: domains A, B and C from different origin and the corresponding domains A', B' and C' in *Arabidopsis thaliana*. x means any amino acid, x in parentheses (x) means an amino acid not required. Brackets denote any one of the amino acid residues in brackets [ ]

PtIPT7a/59-159 is shown as SEQ ID NO: 12
PtIPT7b/1-101 is shown as SEQ ID NO: 13
PtIPT7a/40-141 is shown as SEQ ID NO: 14
Eucgr.G00473/1-102 is shown as SEQ ID NO: 15
Eucgr.G01887/1-102 is shown as SEQ ID NO: 16
AtIPT5/39-140 is shown as SEQ ID NO: 17
PtIPT5b/39-139 is shown as SEQ ID NO: 18
PtIPT5a/39-139 is shown as SEQ ID NO: 19
Eucgr.B01146/1-101 is shown as SEQ ID NO: 20
Eucgr.H03602/40-140 is shown as SEQ ID NO: 21.

Figure 4:
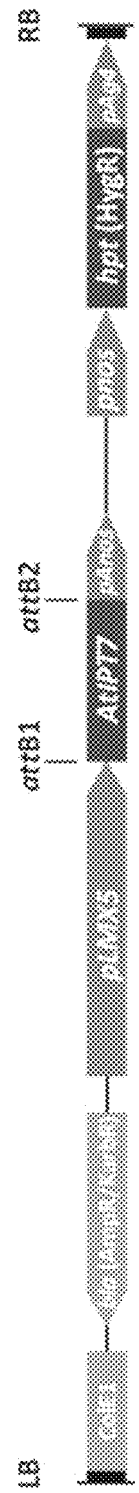

FIG. 4. Part of the transformation vector inserted into the plant genome (ca. 8200 bp). The construct map shows the different sites, together with their origin, estimated size and function.

Figures 5A, 5B, 5C, 5D:
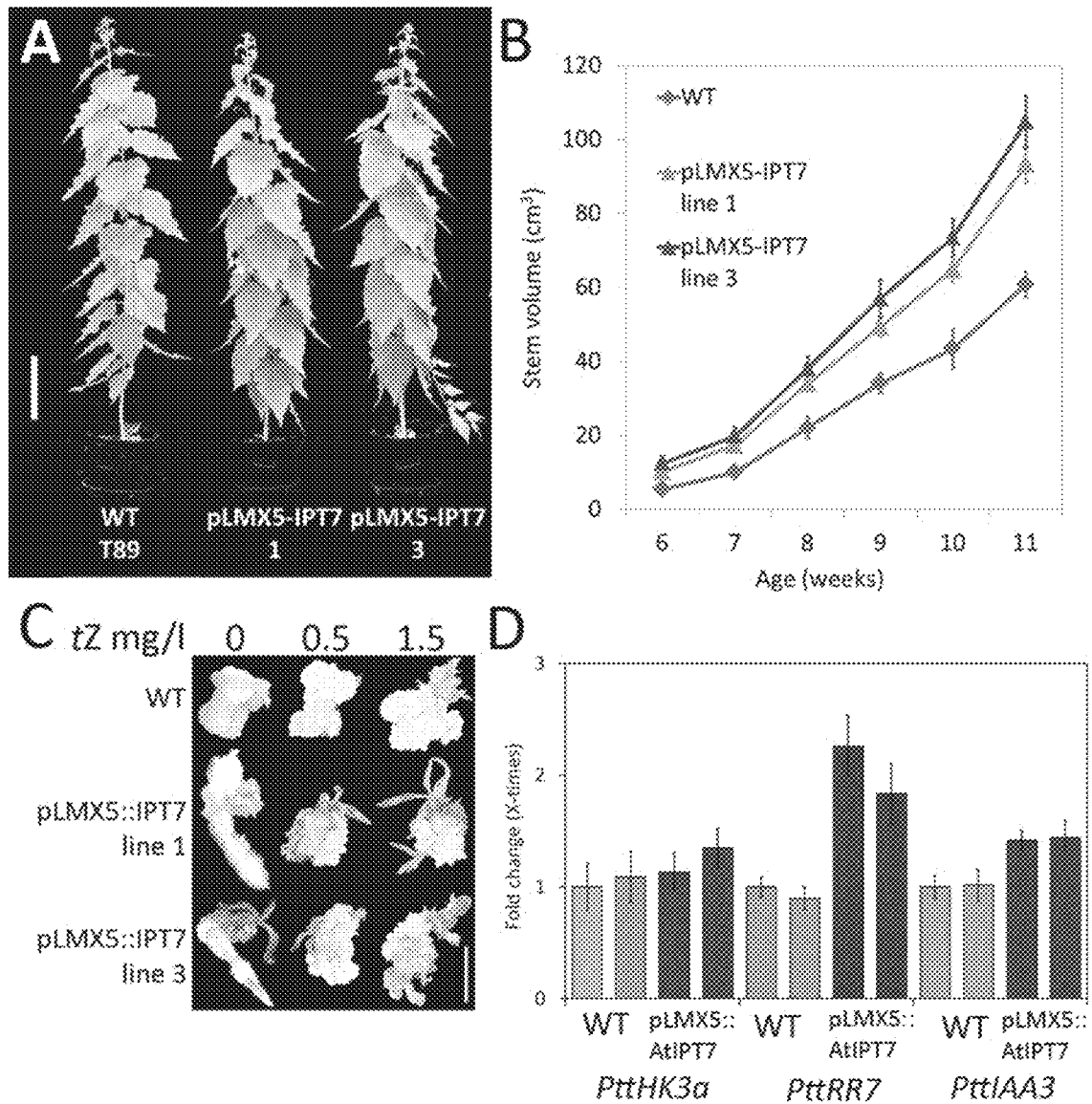

FIG. 5A. Phenotypes of WT and pLMX5-IPT7 line 1 and 3 *Populus* trees in the age of three months.

FIG. 5B. The trunk volume of the transgenic pLMX5-IPT7 *Populus* lines 1 and 3 as compared to the WT.

FIG. 5C. Cytokinin responsiveness assay of the WT and pLMX5-IPT7 lines.

FIG. 5D. Expression of a cytokinin receptor (PttHK3a), a cytokinin signaling primary response gene (type-A RR PttRR7) and an auxin signaling marker gene (PttIAA3) in the WT and pLMX5-IPT7 line 1 stem.

Figure 6:
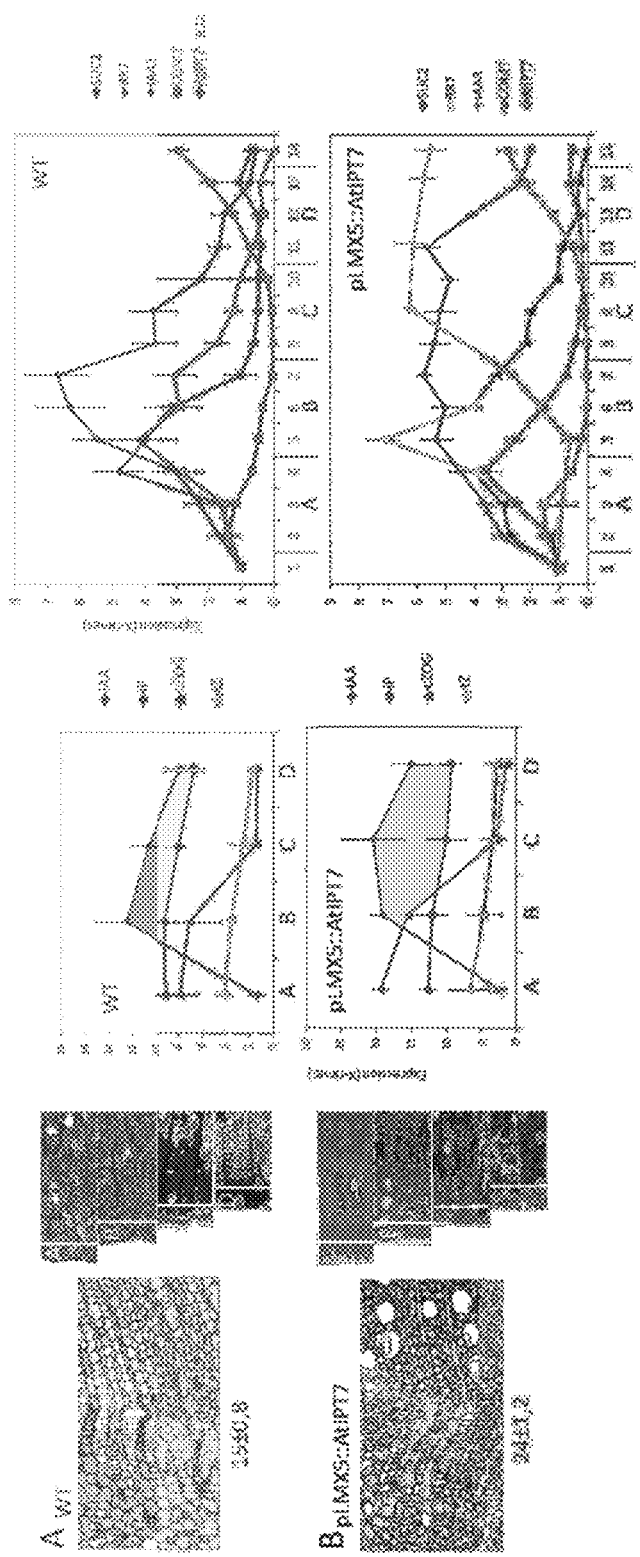

FIG. 6. Cambial anatomy, hormonal content and hormonal signaling profiles of WT (A) and transgenic *Populus* line pLMX5::IPT7 line 1 stem (B). Four fractions (A-D) were collected for the hormonal analysis (A, B).

DETAILED DESCRIPTION OF THE INVENTION

The present invention provides transgenic trees having increased stem volume growth and/or biomass production. Genetic constructs and vectors are described useful in producing said transgenic trees as well as methods used in producing these trees.

The present invention provides a genetic construct comprising a first nucleic acid sequence (effector) encoding cytokinin biosynthetic isopentenyl-transferase enzyme operable linked to a second nucleic acid sequence (promoter) allowing expression of said first nucleic acid sequence in cambial cells.

By "a first nucleic acid sequence" is meant here an effector gene, which encodes cytokinin biosynthetic isopentenyl-transferase enzyme. The first nucleic acid sequence is selected from the group of
(a) a nucleic acid sequence comprising SEQ ID NO:1;
(b) a nucleic acid sequence encoding SEQ ID NO:2;
(c) a nucleic acid sequence encoding an amino acid sequence comprising a conserved domain area A, B and/or C having an amino acid sequence selected from the group of SEQ ID NO:3, 4 and 5;
(d) a nucleic acid sequence encoding an amino acid sequence comprising an area D having at least 80% identity, preferably at least 85% identity, more preferably at least 90% identity, still more preferably at least 95% identity to amino acid sequence SEQ ID NO:6 (i.e. amino acids 40-141 of SEQ ID NO:2; see third line in FIG. 3);
(e) a nucleic acid sequence encoding an amino acid sequence showing at least 80% identity, preferably at least 85% identity, more preferably at least 90% identity, still more preferably at least 95% identity to SEQ ID NO: 2; and
(f) a nucleic acid sequence encoding an enzyme belonging to enzyme class EC 2.5.1.27.

The invention encompasses also embodiments where the first nucleic acid sequence encodes an amino acid sequence comprising a conserved domain area A', B' and/or C' having an amino acid sequence of domain A', B' and/or C' of *Arabidopsis thaliana* as shown in FIG. 2.

Genes encoding cytokinin biosynthetic isopentenyl-transferase enzyme (IPTs) are found in several plant genera and species both in angiosperms and in gymnosperms. When the amino acid sequences of the IPTs have been compared, close homologies have been found in specific domains in different plant genera, see WO 2006/034286. It is therefore possible to find IPTs from different plant genera and species which function in a similar manner as the genes herein described.

Sequence analysis by Kakimoto (2001) of *Arabidopsis* IPTs AtIPT1-9, in comparison with IPTs from *Agrobacterium tumefaciens, Pseudomonas* syringae and *Pantoea agglomerans*, revealed three consensus patterns: domain A (SEQ ID NO:3), domain B (SEQ ID NO:4) and domain C (SEQ ID NO:5). The consensus patterns are shown in FIG. 2, where x denotes any amino acid residue, (x) means an amino acid residue not required, brackets denote any one of the amino acid residues in brackets [ ]. The corresponding domain areas A', B' and C' of 9 different IPTs of *Arabidopsis thaliana* are also shown in FIG. 2.

Figure 1:
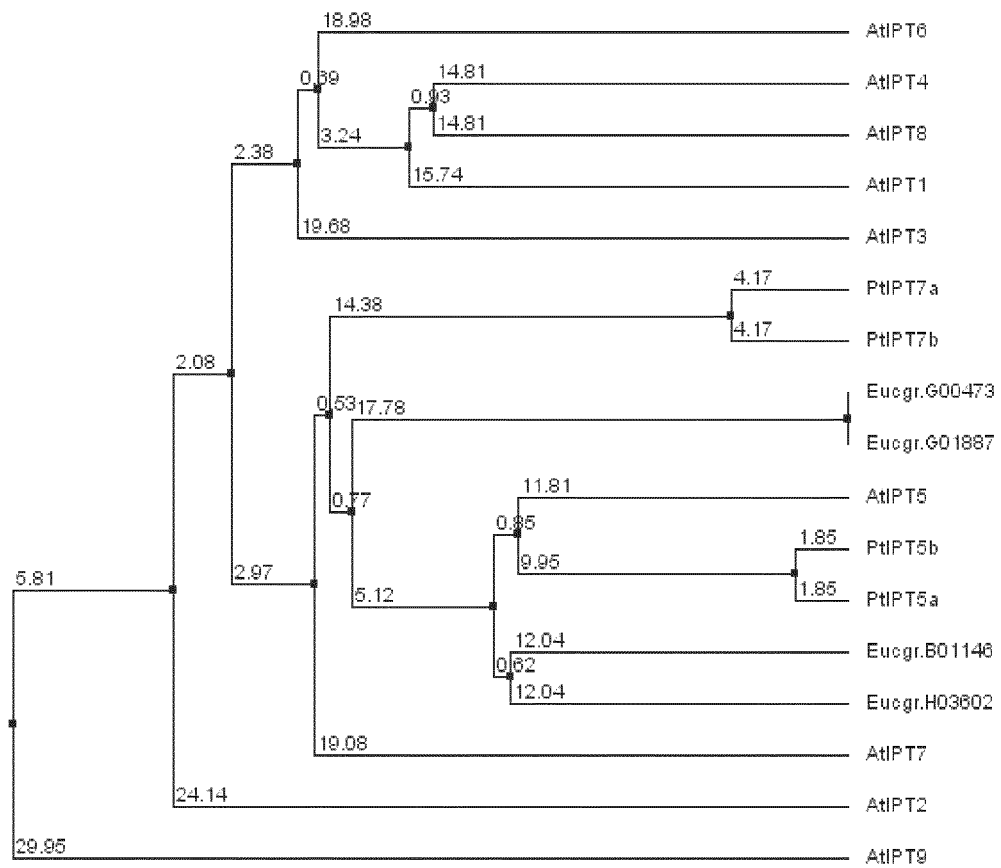
FIG. 1. Phylogenetic tree indicating the average distance of various IPTs, AtIPT5 being the closest *Arabidopsis* ortholog for the AtIPT7.
Figure 3:
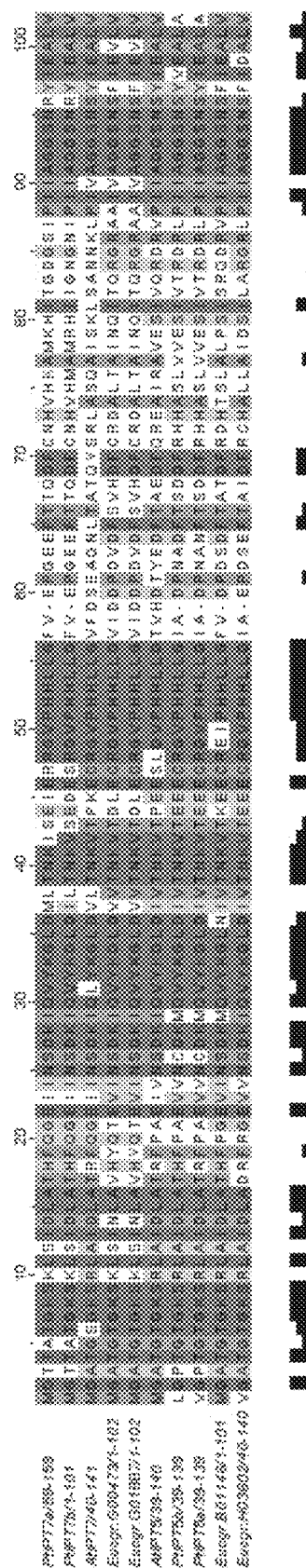
FIG. 3. Comparison of the amino acid sequences of AtIPT7 and AtIPT5 orthologs and the consensus sequence with over 50% similar identity (capital letters indicate amino acids with 100% identical amino acids, whereas lowercase letters indicate identical amino acids in 50-90% of the compared sequences)

Similar conserved domains (shadowed) are present also in the closest AtIPT7 orthologs identified from *Populus trichocarpa* (PtIPT7a eugene3.00041149; PtIPT7b eugene3.00080280; PtIPT5a fgenesh4_pg.C_LG_X000229; PtIPT5b_fgenesh4_pg.C_LG_VIII001825) and *Eucalyptus grandis* (Eucgr.B01146; Eucgr.G00473; Eucgr.G01887; Eucgr.H03602) genomes as shown in FIG. 3.

In the phylogenetic average distance tree AtIPT7 and AtIPT5 have been shown to form a Glade together. AtIPT5 appears to be closest *Arabidopsis* ortholog for the AtIPT7. Between the AtIPT7 orthologs, the consensus sequence, called here consensus area D, with over 50% similar identity is shown in FIG. 3 (capital letters indicate amino acids with 100% identical amino acids, whereas lowercase letters indicate identical amino acids in 50-90% of the compared sequences). In *A. thaliana* IPT7 amino acids 40-141 correspond the conserved sequence, third line in FIG. 3 (in Sequence listing SEQ ID NO: 6).

Methods of alignment of nucleic amino acid sequences are well known for a person skilled in the art, for example Smith-Waterman algorithm (modified for speed enhancements) to calculate the local alignment of two sequences. Blast is the most useful tool for identity determination: Basic Local Alignment Search Tool, or BLAST, is an algorithm for comparing primary biological sequence information, such as the amino acid sequences of different proteins or the nucleotides of DNA sequences. A BLAST search enables a researcher to compare a query sequence with a library or database of sequences, and identify library sequences that resemble the query sequence above a certain threshold. Different types of BLASTs are available according to the query sequences. The BLAST program was designed by Stephen Altschul (Altschul, 1990).

The gene encoding cytokinin biosynthetic isopentenyl-transferase enzyme can be selected among genes encoding different IPTs, preferably from the group of genes encoding IPTs, which belong to enzyme class EC 2.5.1.27.

More preferably the gene encoding cytokinin biosynthetic isopentenyl-transferase enzyme comprise a conserved domain area or areas A, B and/or C having an amino acid sequence or sequences selected from the group of SEQ ID NO: 3, 4 and 5.

Still more preferably the gene encoding cytokinin biosynthetic isopentenyl-transferase enzyme comprise a conserved domain area or areas A', B' and/or C' having an amino acid sequence or sequences of the corresponding domain areas A', B' and/or C' shown in FIG. 2 of 9 IPTs of *Arabidopsis thaliana*.

Still and still more preferably the gene encoding cytokinin biosynthetic isopentenyl-transferase enzyme comprise an area D having at least 80% identity, preferably at least 85% identity, more preferably at least 90% identity, still more preferably at least 95% identity, more and more preferably at least 98% identity, still more preferably at least 99% identity, most preferably 100% identity to amino acid sequence SEQ ID NO:6, (i.e. with the corresponding area in SEQ ID NO:2).

The other areas of the gene encoding cytokinin biosynthetic isopentenyl-transferase enzyme can vary in broader range than the area encoding conserved domain A, B and/or C or A', B' and/or C' and/or area D. The identity % in these areas can be less than 80%, less than 75%, less than 70%, less than 60%, or even less than 50%.

In preferred embodiments of the invention a gene encoding cytokinin biosynthetic isopentenyl-transferase enzyme encodes an amino acid sequence showing at least 80% identity, preferably at least 85% identity, more preferably at least 90% identity, still more preferably at least 95%, more and more preferably at least 98%, still more preferably at least 99% identity, most preferably at least 100% identity to SEQ ID NO: 2.

A gene encoding cytokinin biosynthetic isopentenyl-transferase enzyme can be selected among genes encoding different IPTs, preferably the gene encodes IPT 7 or IPT 5, more preferably IPT7.

A gene encoding cytokinin biosynthetic isopentenyl-transferase enzyme may be derived from any plant genera or species expressing a functional cytokinin biosynthetic isopentenyl-transferase enzyme. Typically the plant is an angiosperm, preferably an *Arabidopsis*, a *Betula*, a *Populus* or a *Eucalyptus* plant.

The effector gene AT3G23630, *Arabidopsis thaliana* isopentenyltransferase 7 (AtIPT7) is from *Arabidopsis*, the gene sequence, and functional analysis of a highly orthologous *Arabidopsis* IPT, AtIPT4, protein has been published by Kakimoto 2001.

The present invention has been exemplified by using *Arabidopsis* cytokinin biosynthetic isopentenyl-transferase enzyme IPT7 encoding gene (gene AT3G23630) SEQ ID NO: 1. Said gene encodes amino acid sequence SEQ ID NO: 2. When the amino acid sequence SEQ ID NO: 2 has been compared with IPTs from other sources, it has been found that close homologies can be found in domain area A, domain area B, and/or in domain area C or between different IPTs in *Arabidopsis thaliana*, it has been found that close homologies can be found in domain area A', domain area B', and/or in domain area C' (see FIGS. 2 and 3). The identity % of these areas between amino acid sequences from different origin is at least 80%, preferably at least 85%, more preferably at least 90%, still more preferably at least 95% even more preferably at least 97%, more and more preferably at least 98%, more and more preferably at least 99%, most preferably 100% identity.

In the present invention it is therefore possible to use genes functioning in similar manner as IPT7 gene from *Arabidopsis*, from several other plant genera and species and/or from different IPTs. It is also possible to use nucleic acid sequences comprising substitutions, insertions, deletions or other modifications compared to SEQ ID NO:1, provided that the nucleic acid sequence encodes cytokinin biosynthetic isopentenyl-transferase enzyme, preferably belonging to enzyme class EC 2.5.1.27. More preferably the enzyme belongs to IPT7.

Nucleic acid sequences encoding cytokinin biosynthetic isopentenyl-transferase enzymes and which are used in the genetic constructs as described herein are typically sequences isolated from their origin, for example *A. thaliana* IPT7 is used in a genetic construct introduced to *Populus* cells to grow a transgenic *Populus* tree. However, it is also possible to enhance the expression of endogenous nucleic acid sequences encoding IPTs.

The genetic construct according to this disclosure comprises a second nucleic acid sequence, which is a promoter allowing expression of cytokinin biosynthetic isopentenyl-transferase enzyme in meristematic cells of a plant. Preferably the promoter allows expression in cambial cells and apical cells, more preferably specifically in cambial cells.

By "a promoter" is meant a DNA region binding RNA polymerase and directing the enzyme to the appropriate transcription initiation site for a particular polynucleotide sequence. A promoter may additionally comprise other recognition sequences referred to as upstream promoter elements, which influence the transcription initiation rate.

An example of a promoter allowing expression in meristematic cells in cambium and in apical cells is birch meristem promoter pBpCRE1. The promoter is preferably defined by SEQ ID NO: 7 (GenBank EU583454, Nieminen et al. 2008).

Another example of a promoter allowing expression in meristematic cells is a promoter allowing expression specifically in cambial cells. Such specifically in cambial cells expressing promoter is *Populus* cambial specific promoter pLM5, preferably defined by SEQ ID NO: 8 (pLM5 promoter is described also in WO2004097024A1 as SEQIDNO4 LMX5 A055P19U).

In the genetic construct the first nucleic acid sequence (effector) is operable linked to the second nucleic acid sequence (promoter). By "operable linked" is meant that two genetic elements are linked by a functional linkage, for example an effector gene is operable linked to a promoter allowing expression of the effector gene.

A genetic construct can contain also a selectable marker for the selection of cells comprising the introduced genetic construct. Selectable markers are for example antibiotic resistances ampicilline, carbenicilline and hygromysin B resistance.

In the present disclosure the linking of promoter and effector has been exemplified by promoter pLMX5, which has been operably linked to the effector gene by inserting it into the close proximity of the effector gene in the Gateway $2^{nd}$ box cloning site (FIG. 4)

The following Gateway cloning primers have been used:

```
IPT7_Fwd GW primer:
                            (SEQ ID NO: 9)
ACAAAAAAGCAGGCTTAATGAAGTTCTCAATCTCA IPT7_REV GW primer:
                            (SEQ ID NO: 10)
TACAAGAAAGCTGGGTATCATATCATATTGTGGG
```

When the LMX5::AtIPT7 construct (SEQ ID NO:11) has been introduced into trees, transgenic trees with the LMX5::AtIPT7 construct display ectopic overexpression of *Arabidopsis thaliana* adenosine phosphate-isopentenyl-transferase 7(IPT; EC 2.5.1.27), expressed in the cambial zone through the LMX5 promoter (described in Love et al. 2009). In the transgenic trees, cytokinin signaling has been stimulated by increasing the amount of cytokinin plant hormone in the cambial zone. Adenosine phosphate-isopentenyltransferase 7 (AtIPT7) enzyme from *Arabidopsis thaliana* catalyzes the first (rate-limiting) reaction in the biosynthesis pathway of isoprene cytokinins. AtIPT7 is expressed at the vascular tissue in *Arabidopsis* (Sakakibara, 2006).

In FIG. 4 are presented the following regions:
LB Left Border: *Agrobacterium tumefaciens;* 25 bp; recognition site for the virulence genes in the Ti-plasmidin; start of the insert (part of the plasmid transferred into the plant genome). Start position the $1^{st}$bp.ColE1 (replicon): part of *Escherichia coli* pBR322 plasmid; 615 bp; amplification of the bacterial cultures (not expressed in the transgenic plants);
β-lactamase(bla)-gene: part of *E. coli* pBR322 plasmid; 861 bp; gene gives an ampicilline/carbenicillineresistance in bacterial cultures (not expressed in the transgenic plants);
pLMX5: hybrid aspen (*Populus* tremula×*P. tremuloides*); 1807 bp; promoter used for the overexpression of the adenosine phosphate-isopentenyl-transferase 7 (AtIPT7) enzyme gene. Start position the 3000th bp.
attB1: synthetic (Invitrogen-company); 19 bp; recombination site in the Gateway-technique;
Gene coding for Adenosine phosphate-isopentenyltransferase 7 (AtIPT7)enzyme: *A. thaliana;* 990 bp. Start position 4858th bp.
attB:; synthetic (Invitrogen-company); 17 bp; recombination site in the Gateway-technique;
pAnos (non-coding 3'region of the nopaline synthase-gene): *A. tumefaciens; ca.* 200 bp[(1)]; polyadenylation signal (signal for the end of the transcription) for the ERF-genes;
pnos, *A. tumefaciens;* ca. 200 bp[(1)]; promotor for hygromycinphosphotransferase (hpt)-gene expression;
hpt; *E. coli;* 1000 bp[(1)]; gene gives a resistance for the hygromysin B used for the selection;
pAg4 ($T_L$-DNA:n gene 4): *A. tumefaciens;* about 200 bp[(1)]; polyadenyation signal for the hpt-gene
RB ('Right border'): *Agrobacterium tumefaciens;* 25 bp; recognition region of the virulence genes in the Ti-plasmid; end of the plant genome insert. [(1)] In the original reference articles (Walden et al., 1990; Koncz et al., 1994) the size of the site is not defined, and it cannot be deduced from other sources.
Backbone vector similar to *Agrobacterium* binary gap repair vector pGAPHyg, (complete sequence: Sequence ID: gbIEU933993.1, length: 7942) and to pBR322.

To introduce the genetic construct into a plant a vector is usually needed. Suitable vector is for example bacterium *Agrobacterium tumefaciens.*

There are also other systems available for introducing genetic material to plants. Such systems do not necessarily need vector. It is possible for example to introduce genetic material to angiosperm and gymnosperm species through sexual reproduction between trees and by particle bombardment (DNA covered gold particles are shot into cells).

The present invention provides a tree, which overexpresses an endogenous nucleic acid sequence encoding cytokinin biosynthetic isopentenyl-transferase enzyme, or expresses an exogenous nucleic acid sequence encoding cytokinin biosynthetic isopentenyl-transferase enzyme.

As described herein the effector gene needs to be expressed in cambial cells. This is possible by using a promoter allowing expression in meristematic cells generally. However, it is of disadvantage, if the cell division is enhanced in any meristematic cells. If for example the leaves of a tree are grown very large or tight that may of disadvantage, although the stem volume is increased at the same time. According to the present disclosure a promoter allowing expression in cambial cells and apical cells is preferably used, since the overall growth of the tree is not huge, only the stem volume growth and growth of the height. Most preferably a promoter is used, allowing expression specifically in cambial cells. In this case the stem volume growth is increased, but not the overall growth of the tree and not either the height of the tree is increased. All the comparisons are meant to be made to a wild type tree of the same species, age and growth conditions.

The effector gene can be introduced to a tree by using the genetic construct as described herein. Alternatively, the expression of an effector gene being endogenous to a tree can be improved. For example in *Populus* the expression of *Populus* IPT 7 can be improved.

Expression of the gene can be enhanced through ectopic overexpression, by driving the endogenous gene as through an alternative promoter, driving a higher expression level than the endogenous promoter. This can be done by introducing a novel copy of the endogenous gene, under the chosen promoter, into the genome. Alternatively, expression of the endogenous gene can be enhanced through activation tagging, where enhancer elements are introduced into plant genome, where they are able to enhance transcription of genes in their proximity. In the future, enhanced expression of the endogenous gene may also be attained through genome editing, e.g. with engineered nucleases, which can be used to delete silencor elements repressing expression of the desired genes.

A transgenic tree produced as described herein expresses at least 40%, preferably at least 44%, more preferably at least 46%, still more preferably at least 50%, more and more preferably at least 60% higher levels of cytokinin signaling in cambial cells during cambial development compared to a WT tree.

Furthermore, in a transgenic tree produced as described herein the stem volume growth in said tree is at least 35% higher, preferably at least 38%, more preferably at least 40%, still more preferably at least 45%, more and more preferably at least 50% higher compared to wild type (WT) tree.

In one aspect of the invention, the tree expressing an effector gene in cambial cells belongs preferably to angiosperms. The tree is an annual tree or a perennial tree, preferably a perennial tree. The tree belongs to genera *Betula*, *Populus* or *Eucalyptus*. Preferably the tree belongs to genus *Populus*. The *Populus* is selected from the group of *Populus* species *P. tremula*, *P. alba*, *P. tremuloides*, *P. canescens*, *P. deltoids*, *P. fremontii*, *P. nigra*, *P. Canadensis*, *P. inopina* and *Populus tremula×tremuloides*. The function of the construct has been tested and confirmed in the hybrid aspen, *Populus tremula×tremuloides*.

In second aspect of the invention the tree expressing an effector gene in cambial cells belongs to gymnosperms. The tree is preferably spruce or pine.

The present invention encompasses also various wood products obtainable from the transgenic trees of the invention. Such wood products are for example trunks, branches, roots and seeds.

The present invention provides also a method for producing a transgenic plant capable of increased biomass production and/or increased stem volume growth compared to wild type plant. The method comprises the steps of
    introducing a nucleic acid sequence encoding cytokinin biosynthetic isopentenyl-transferase enzyme operationally linked to a promoter allowing expression in cambial cells, to a tree cell,
    cultivating said cell to form a cell culture,
    regenerating the cell culture to a plant, in which the nucleic acid sequence encoding cytokinin biosynthetic isopentenyl-transferase enzyme is expressed in cambial cells during cambial development.

*Agrobacterium* based transformation methods for angiosperm trees have been published by e.g. Häggman et al. 2003, Seppänen et al. 2004 and Nilsson et al. 1992. In general the method comprises that plants explants (leaf discs, stem segments, etc.) are incubated in an *Agrobacterium* culture, after which they are co-cultured with *Agrobacterium* bacteria on a solid culture medium. To end the co-culture, *Agrobacterium* bacteria are removed by washing. Plants explants are grown on a callus production medium supplemented by an antibiotic to limit the callus production to transgenic cells harbouring the antibiotic resistance gene. The forming callus tissues are transferred onto a regeneration medium for shoot production. The regenerated shoots are transferred onto a root induction medium. After the roots are formed, the plantlets can be grown in soil.

The present invention provides also a method for improving the production of biomass and/or increased stem volume growth in trees. The method comprises the steps of
    introducing a nucleic acid sequence encoding cytokinin biosynthetic isopentenyl-transferase enzyme operationally linked to promoter allowing expression in cambial cells, to a tree cell,
    cultivating said cell to form a cell culture,
    regenerating the cell culture to a plant, in which the gene encoding cytokinin biosynthetic isopentenyl-transferase enzyme is expressed in cambial cells during cambial development,
    allowing said plant to grow to an adult tree having enhanced radial growth compared to wild type tree.

In *Agrobacterium* mediated transformation plant explants are co-cultured with *Agrobacterium* bacteria containing the desired transgene. *Agrobacterium* bacteria will transform plant cells in the explants through the integration of transgenic DNA into the plant genome. Placed on selectable rooting and shooting media, transgenic plants will be regenerated from the transformed cells.

In particle (microprojectile) bombardment method particles of gold or tungsten are coated with DNA and shot into plant cells. Inserted DNA will integrate into the plant genome.

In electroporation method transient holes are formed in plant protoplast membranes using electric shock; this allows transgene DNA to enter plant protoplasts.

In viral transformation (transduction) method the desired transgene is packaged into a suitable plant virus, and the plant is infected by this virus. The transgenic material will integrate into the plant genome.

By "increased biomass production" is meant here the additional amount of biomass (stem dry weight mass) of transgenic trees compared to wild type trees at the same age.

In this description stem dry mass of WT trees was measured at the age of 16 weeks (average of 3 trees) and was 35±2 (STDEV) g, whereas the stem of pLMX5-IPT7 trees (3 trees) was 51±8 g.

By "increased stem volume growth" is meant here the additional amount of stem volume in transgenic trees compared to wild type trees at the same age.

In this description stem volume was measured once per week, 3 measurements points (10 cm above soil level, middle tree, 2 cm below apex), volume was calculated by formula of fructa (sum of basal to middle and middle to apex).

$$V = \frac{\pi h}{3}(r^2 + rR + R^2)$$

wherein V=volume
h=height
r=radius of upper part
R=radius of lower part
http:www.mathwords.com/f/frustum.htm.

Transgenic IPT7 overexpressing trees had more stem volume compared to WT trees (FIG. 5). The stem volume growth in transgenic trees was in average 53% higher, and at least 38% higher, if standard errors were taken into account.

Transgenic trees expressed in average 83% and at least 44%, if standard errors were taken into account, higher levels of cytokinin signaling in cambial cells during cambial development compared to WT trees.

The present invention encompasses also applications where the transgenic tree is sterile tree not capable of flower, pollus or seed development. Methods used to produce sterile trees are known for a person skilled in the art.

Sterile clones of hybrids between two related species with different chromosome numbers (tetraploid crossed with diploid to make a sterile triploid for example) can be selected for transformation. Transgenic trees can be clonally propagated and tested for their sterility (for abolished, aborted or sterile flower, pollen or seed development).

To exemplify the present invention the engineering of transgenic trees displaying an elevated cytokinin signaling level is described herein. Of these trees the status and pattern of auxin and cytokinin distribution and signaling were analyzed.

The concentration of auxin and cytokinin profiles across the cambial meristem in *Populus* stem was characterized. Furthermore, to correlate the cytokinin hormonal profiling with cytokinin signaling, an extensive analysis of the expression profiles of cytokinin biosynthetic and signaling genes across the *Populus* cambial zone was made.

To better understand the interaction between two major hormonal pathways, cytokinin and auxin, in the regulation of cambial cell divisions, their concentration levels across the cambial zone of *Populus trichocarpa* stem were analyzed. Stem cryosections representing phloem, conducting phloem, developing phloem, cambium, developing xylem and xylem tissues (FIG. 6) were analyzed.

To verify the tissue identity of analyzed cryosections, marker genes for various tissue types were included in the analysis. PtSUC2 was used as a phloem cell marker, PtANT, as a marker for dividing cambial cells, and PtCOMT2 for phloem fibers and xylem cells. The markers correlated well with the identity of the tissues determined through microscopy during the cryo-sectioning.

The present invention is based on a detailed analysis of cytokinin function in the regulation of cambial development in a tree stem. In a manner similar to auxin, also cytokinin hormone has a concentration gradient across the cambial zone. The cytokinin concentration peak coincides with the high expression domain of biosynthetic and signaling genes of this hormone.

With the exception of PtCKI1 genes, expression of all components of the cytokinin biosynthesis and signal transduction pathway in the *Populus* cambium was detected. Either the effective expression level of the CKI1 genes is very low, below the detection limit of the expression analysis, or they are not required for cambial development during the active growth of *Populus* trees.

The expression of all components of cytokinin signaling confirms the importance of this hormonal signaling pathway for the activity of vascular cambium.

Interestingly, the cambial distribution profile of cytokinin is distinct, but partially overlapping with, the concentration profiles of auxin. The high auxin concentration is restricted at the domain of actively dividing, undifferentiated cambial cells; whereas the high cytokinin concentration has a larger domain extending from the undiffereted cambium to the developing phloem.

In this disclosure has been shown that biomass accumulation in tree stem can be enhanced by stimulating cytokinin signaling in the transgenic *Populus* trees. These trees displayed enhanced cytokinin responsiveness together with an elevated level of cytokinin signaling. The cambial cell division activity of the transgenic trees was increased as compared to the WT trees, and respectively the radial growth of the stem was accelerated. As these trees were of WT height, the stimulatory effect of cytokinin on the radial growth was independent of the apical growth rate. Furthermore, this stimulative action of cytokinin appeared to take place through crosstalk between CK and auxin: an elevated CK concentration and signaling increased the level and widened the domain of auxin concentration and signaling in the cambial region. Potentially the partially overlapping domains of auxin and cytokinin action have specific functions in the regulation of different developmental processes taking place across the cambial zone. Cross-talk between auxin and cytokinin at the middle of the cambium may define the stem cell niche for the maintenance of an actively dividing cell pool. Respectively, possibly the high cytokinin to auxin ratio at the phloem side of the cambial zone contributes to the determination of the phloem identity of the developing vascular cells.

The invention is illustrated by the following non-limiting examples. The invention is applicable to other genes, genetic constructs and plants than those illustrated in examples. It should be understood, however, that the embodiments given in the description above and in the examples are for illustrative purposes only, and that various changes and modifications are possible within the scope of invention.

EXAMPLES

Example 1

Engineering of transgenic *Populus* trees with stimulated cambial cytokinin signaling To study the effect of cytokinin signaling on stem growth, transgenic *Populus* (*P. tremula*x*tremuloides*) trees were engineered to display elevated cytokinin signaling during cambial development. To stimulate biosynthesis, AtIPT7 gene from *Arabidopsis* encoding a cytokinin biosynthetic isopentenyltransferase was used. The AtIPT7 was expressed under the cambial specific PttLMX5 promoter (Love et al. 2009), which shows a high expression in the cambial and developing xylem cells.

Several separate transgenic lines with the LMX5::IPT7 construct were obtained showing a detectable AtIPT7 expression. No AtIPT7 expression was detected in the untransformed lines. Two lines (AtIPT7 1 and 3) with a high transgene expression level were selected for further analyses.

Example 2

Accelerated Radial Growth of the Tree Trunk in the Transgenic Lines

To evaluate the effect of AtIPT7 activity on tree development, growth dynamics of the transgenic trees was studied under greenhouse conditions (FIG. 5A). The apical growth rate of the pLMX5::AtIPT7 lines was similar to wild-type plants; the transgenic plants had the same height as the controls at the same age (FIG. 5A). In contrast, the diameter of the stem was increased in the transgenic trees as compared to the WT trees. Respectively the stem volume, which was counted as the additive volume of internodes without the leaves, was larger than that of the WT trees (FIG. 5B).

FIG. 5A shows the phenotypes of WT and pLMX5-IPT7 line 1 and 3 *Populus* trees in the age of three months. All trees had similar height.

FIG. 5B shows the trunk volume of the transgenic pLMX5-IPT7 *Populus* lines 1 and 3 as compared to the WT. The total stem volume of the transgenic lines was increased as compared to the WT. Values are averages (±SD) from five individual trees per each line.

Example 3

Enhanced Cytokinin Responsiveness of the Transgenic Lines

To evaluate the effect of cambial AtIPT7 expression on cytokinin signaling, cytokinin responsiveness of the transgenic trees was tested. In the classic cytokinin responsiveness assay (Skoog & Miller 1957), a low cytokinin-to-auxin ratio induces root regeneration from plant segments and a high cytokinin-to-auxin ratio promotes instead shoot regeneration. In this assay, shoot segments were cut from greenhouse grown transgenic and WT lines, and then grown in in vitro conditions on a medium with a varying concentration of trans-Zeatin (tZ).

In the assay, a majority of the stem segments from the IPT7 lines produced shoots even in the 0.5 mg/l tZ concentration, whereas only a few WT samples were able to do so (FIG. 5C). This result indicates that the transgenic lines display an elevated basal level of cytokinin signaling, as even a moderate concentration of applied cytokinin can induce shoot production; a typical cytokinin response phenotype. Additionally, the transgenic lines produced roots on the medium with 0 mg/l tZ. As auxin, together with cytokinin, promotes root formation, the result indicates that these lines may have had both more cytokinin and auxin than the control trees.

FIG. 5C depicts cytokinin responsiveness assay of the WT and pLMX5-IPT7 lines. Stem segments were grown on a medium with 0.5 mg/L auxin (IAA) and 0, 0.5 or 1.5 mg/L cytokinin t-zeatin. Transgenic lines regenerated shoots already in low cytokinin concentrations (0.5 mg/L), whereas WT required a higher (1.5 mg/L) concentration of this hormone.

Example 4

Elevated Cambial Cytokinin Signaling Levels in the Transgenic Trees

The status of cambial cytokinin signaling in the transgenic trees was studied. The expression levels of two cytokinin marker genes were analyzed. Two marker genes were used to evaluate the cytokinin signaling level: a cytokinin receptor PttHK3a and a type-A response regulator PttRR7. The level of auxin signaling was studied through an auxin signaling marker gene (PttIAA3). The PttRR7 represents a primary response gene of cytokinin phosphorelay: expression of A-type response regulator genes is upregulated by cytokinin signaling: the expression level of this gene reflects the level of cytokinin response taking place in the analyzed trees. In the IPT7-lines the expression of cytokinin receptor PttHK3a was essentially the same as in the WT trees whereas the expression levels of PttRR7 and PttIAA3 were elevated (FIG. 5D).

FIG. 5D depicts the expression of a cytokinin receptor (PttHK3a), a cytokinin signaling primary response gene (type-A RR PttRR7) and an auxin signaling marker gene (PttIAA3) in the WT and pLMX5-IPT7 line 1 stem. The expression levels of PttRR7 and PttIAA3 were elevated in the pLMX5-IPT7 line as compared to WT, whereas the expression of PttHK3a was not affected. Two individual trees per line were analyzed by qRT-PCR (error bars=SD).

This result shows that the level of cytokinin and auxin signaling was successfully elevated through an elevated CK concentration, whereas the capacity for cytokinin perception had not been modified.

Example 5

Increased Number of Cambial Cell Divisions in the Transgenic Trees

To study the effect of elevated cytokinin signaling on the vascular architecture, the cambial anatomy of transgenic trees was analyzed. Meristematic undifferentiated cambial cells were defined in the cross-sections as the small and flat, thin-walled cells localized in the cambial cell files between the differentiating xylem and phloem cells. The first differentiating xylem and phloem cells were defined as having a larger and more round size. In the IPT7-trees, the vascular cambium contained more meristematic cells in the cambial cell files than the WT trees (24 vs 15) (FIG. 6A-B). Based on the increased cell number, it can be concluded that the cambial cell files were undergoing additional cell divisions, as compared to the WT.

Furthermore, it was studied if, in addition of stimulating the cell division rate, the elevated cytokinin signaling level also affected the morphology of the produced xylem cells. To find this out, the dimensions of the xylem cells, vessels and fibers was analyzed, in macerated stem samples. As compared to the WT trees, the length and width of the xylem cells in the IPT7-trees was not significantly different.

Example 6

Elevated cytokinin signaling affects cambial auxin signaling domain

Next it was studied how the hormonal regulation of cambial meristem reacts to an elevated cytokinin concentration. To study this, the cambial hormone signaling dynamics was profiled through a hormone concentration and marker gene expression studies. The concentrations of bioactive iP and tZ were almost 30% higher in the transgenic trees, whereas the IAA and cZOG concentrations were doubled. Notably, the cytokinin distribution profiles were generally similar between the WT and transgenic line, whereas the shape of auxin distribution was different. Transgenic tree had a wider domain of high auxin concentration: the IAA level was higher in developing xylem and xylem cells than in the WT.

To connect the hormonal profiles with signaling pattern, the expression pattern for auxin and cytokinin signaling marker genes was characterized across the cambial zone. PttRR7 was used as a marker for cytokinin and PttIAA3 for auxin signaling. Similar to the hormone concentration study, cryo-sections representing phloem, developing phloem, cambium, developing xylem and xylem, were analyzed. The PttSUC2 and PttCOMT were used as marker genes for phloem and phloem fibers and xylem cells, respectively, to confirm the identity of the sections. Two wild-type trees and two IPT7 trees were analyzed. In both transgenic and WT trees, the RR7 expression peaks in the developing phloem tissue, where also the phloem marker PtSUC2 has high expression (FIG. 6). Cambium, where the phloem and xylem markers have low expression levels, displays high IAA3 and rising RR7 expression levels. Developing xylem tissue has high IAA3 and a rising COMT expression, whereas in maturing xylem only the xylem marker expression is high.

When the WT and transgenic trees were compared, it can be seen that the IPT7-trees have a wider domain of high auxin signaling. The cambium, which is a domain of high RR7 and IAA3 expression, and developing xylem, a domain of high IAA3 and moderate RR7 expression, tissues are larger in the transgenic lines as compared to the WT tree (FIG. 6). This widened domain of auxin signaling corresponds with the increase in the number of meristematic cells.

Cambial anatomy, hormonal content and hormonal signaling profiles of WT (A) and transgenic Populus line pLMX5::IPT7 line 1 stem (B) are shown in FIG. 6. In the IPT7-trees, the vascular cambium contained more meristematic cells in the cambial cell files than in the WT trees (24 vs 15). Four fractions (A-D) were collected for the hormonal analysis. In WT, the 4$^{th}$ fraction represents fully developed xylem cells, whereas in pLMX5::IPT7 it still contains developing xylem cells, indicating that the meristematic cambial zone is wider in the pLMX5::IPT7 stem than in WT.

The hormonal profiles of auxin (IAA) and bioactive cytokinins (iP and tZ) together with a cytokinin storage form (cZOG) were analyzed in four cambial fractions (A-D). The concentrations of bioactive cytokinins iP and tZ were almost 30% higher in the transgenic trees, whereas the IAA and cZOG concentrations were doubled. Notably, cytokinin distribution profiles were generally similar between the WT and transgenic line, whereas the shape of auxin distribution was different. Transgenic tree had a wider domain of high auxin concentration (highlighted by grey shading).

To correlate the hormonal profiles with signaling domains, expression patterns of marker genes were analyzed by qRT-PCR in fourteen cryosections from phloem (1) into the xylem (14) tissues. The letters under the graph indicate the position of the four hormone analysis fractions (A-D). PttSUC2 was used as a phloem marker, a cytokinin primary response gene PttRR7 as a CK signaling marker, PttIAA3 as an auxin signaling marker, and PttCOMT2 as a phloem fiber and xylem identity marker. Based on the PttRR7 expression, the cytokinin signaling level was elevated in the pLMX5::IPT7 tree. The width of high cytokinin concentration domain (fractions 3-7 in both WT and pLMX5::IPT7) was instead not affected. In contrast, the cambial domain with high auxin marker gene expression and decreasing cytokinin marker gene expression (WT fractions 5-7 vs pLMX5::IPT7 fractions 5-11) was wider in the transgenic line than in the WT tree (3 vs 7 fractions). The level of transgene AtIPT7 expression was below detection limit in WT, whereas had a high expression at the cambial zone of the pLMX5::IPT7 tree.

REFERENCES

Altschul S F; Gish W; Miller W; Myers E W; Lipman D J. 1990. Basic local alignment search tool. National Center for Biotechnology Information, National Library of Medicine, National Institutes of Health, Bethesda, Md. 20894. J Mol Biol 215: 403-10 (1990)

El-Showk S, Ruonala R, Helariutta Y. 2013. Crossing paths: cytokinin signalling and crosstalk. Development. April; 140(7):1373-83. doi: 10.1242/dev.086371.

Häggman H, Frey A D, Aronen T, Ryynänen L, Julkunen-Tiitto R, Tiimonen H, Pihakaski-Maunsbach K, Jokipii S, Chen X, Kallio P T. 2003. Expression of Vitreoscilla hemoglobin in hybrid aspen (Populus tremula×tremuloides). Plant Biotechnology Journal 1: 287-300.

Kakimoto T. Identification of plant cytokinin biosynthetic enzymes as dimethylallyl diphosphate:ATP/ADP isopentenyltransferases. Plant Cell Physiol. 2001 July; 42(7): 677-85.

Koncz C, Martini N, Szabadosz L, Hrouda M, Bachmair A, Schell J (1994) in Plant Molecular Biology Manual, edsGelvin S B, Schilperoort R A, Verma DPS (Kluwer, Dordrecht, The Netherlands), Vol B2, pp 1-22.

Love J, Björklund S, Vahala J, Hertzberg M, Kangasjärvi J, Sundberg B. 2009. Ethylene is an endogenous stimulator of cell division in the cambial meristem of Populus. Proceedings of the National Academy of Sciences, USA 106: 5984-5989.

Nieminen K, Immanen J, Laxell M, Kauppinen L, Tarkowski P, Dolezal K, et al. Cytokinin signalling regulates cambial development in poplar. Proc Natl Acad Sci USA 2008; 105:20032-7.

Nilsson et al. 1992. Spatial pattern of cauliflower mosaic virus 35S promoter-luciferase expression in transgenic hybrid aspen trees monitored by enzymatic assay and non-destructive imaging. Transgenic Research 1: 209-220.

Sakakibara (2006). Cytokinins: activity, biosynthesis, and translocation. Annual Review of Plant Biology 57:431-449.

Seppänen S K, Syrjälä L, von Weissenberg K, Teeri T H, Paajanen L, Pappinen A. 2004. Antifungal activity of stilbenes in in vitro bioassays and in transgenic Populus expressing a gene encoding pinosylvin synthase. Plant Cell Reporter 22: 584-93.

Skoog F., Miller C. O. (1957). Chemical regulation of growth and organ formation in plant tissue cultures in vitro. Symp. Soc. Exp. Biol. 11: 118-131.

Tuskan et al. (2006). Science. 313(5793):1596-604.

Walden R, Koncz C, Schell J (1990) The use of gene vectors in plant molecular biology. Methods in Molecular and Cellular Biology 4: 175-194.

The invention claimed is:

1. A genetic construct comprising or having contained therein a first nucleic acid encoding a polypeptide having cytokinin biosynthetic isopentenyl-transferase enzyme activity operably linked to a second nucleic acid comprising a promoter active in a cambial cell to allow expression of said first nucleic acid in the cambial cell,
wherein said first nucleic acid has at least about 95% sequence identity to SEQ ID NO:2; and
wherein said second nucleic acid sequence comprises a birch meristem promoter pBpCRE1 comprising a sequence having at least 95 % sequence identity to SEQ ID NO: 7.

2. The genetic construct according to claim 1, wherein said first nucleic acid sequence encodes an adenosine phosphate-isopentenyltransferase enzyme 7, IPT7.

3. The genetic construct according to claim 1, wherein said first nucleic acid sequence is derived from an *Arabidopsis*.

4. A genetic construct comprising or having contained therein a first nucleic acid encoding a polypeptide having cytokinin biosynthetic isopentenyl-transferase enzyme activity operably linked to a second nucleic acid comprising a promoter active in a cambial cell to allow expression of said first nucleic acid in the cambial cell,
wherein said first nucleic acid has at least about 95% sequence identity to SEQ ID NO:2; and
wherein said second nucleic acid sequence comprises a cambial specific promoter comprising a sequence having at least 95% sequence identity to SEQ ID NO:8.

5. The genetic construct according to claim 4, wherein said promoter comprises a *Populus* cambial specific promoter pLM5.

6. A vector comprising or having contained therein a genetic construct according to claim 1.

7. The genetic construct according to claim 5, wherein said *Populus* cambial specific promoter pLM5 has a sequence as set forth SEQ ID NO:8.

8. The genetic construct of claim 1, wherein said first nucleic acid has at least about 95% sequence identity to SEQ ID NO:2, and comprises a nucleic acid sequence encoding an amino acid sequence comprising a conserved domain area A, B and/or C, wherein conserved domain A comprises an amino acid sequence having at least 95% sequence identity to SEQ ID NO:3, wherein conserved domain B comprises an amino acid sequence having at least 95% sequence identity to SEQ ID NO:4, and wherein conserved domain C comprises an amino acid sequence having at least 95% sequence identity to SEQ ID NO:5.

9. The genetic construct of claim 1, wherein said first nucleic acid has a sequence as set forth in SEQ ID NO:2.

10. A genetic construct comprising or having contained therein a first nucleic acid encoding a polypeptide having cytokinin biosynthetic isopentenyl-transferase enzyme activity operably linked to a second nucleic acid comprising a promoter active in a cambial cell to allow expression of said first nucleic acid in the cambial cell,
wherein said first nucleic acid comprises a nucleic acid sequence encoding an amino acid sequence comprising a conserved domain area A, B and/or C, wherein conserved domain A comprises an amino acid sequence having at least 95% sequence identity to SEQ ID NO:3, wherein conserved domain B comprises an amino acid sequence having at least 95% sequence identity to SEQ ID NO:4, and wherein conserved domain C comprises an amino acid sequence having at least 95% sequence identity to SEQ ID NO:5, and wherein said first nucleic acid sequence encodes an adenosine phosphate-isopentenyltransferase enzyme 7, IPT7 or an adenosine phosphate-isopentenyltransferase enzyme 5, IPT5; and wherein said second nucleic acid sequence comprises a birch meristem promoter pBpCRE1 comprising a sequence having at least 95% sequence identity to SEQ ID NO: 7.

11. The genetic construct according to claim 10, wherein said first nucleic acid sequence encodes an adenosine phosphate-isopentenyltransferase enzyme 7, IPT7.

12. The genetic construct according to claim 10, wherein said first nucleic acid sequence is derived from an *Arabidopsis*.

13. A genetic construct comprising or having contained therein a first nucleic acid encoding a polypeptide having cytokinin biosynthetic isopentenyl-transferase enzyme activity operably linked to a second nucleic acid comprising a promoter active in a cambial cell to allow expression of said first nucleic acid in the cambial cell, wherein said first nucleic acid comprises a nucleic acid sequence encoding an amino acid sequence comprising a conserved domain area A, B and/or C, wherein conserved domain A comprises an amino acid sequence having at least 95% sequence identity to SEQ ID NO:3, wherein conserved domain B comprises an amino acid sequence having at least 95% sequence identity to SEQ ID NO:4, and wherein conserved domain C comprises an amino acid sequence having at least 95% sequence identity to SEQ ID NO:5, and wherein said first nucleic acid sequence encodes an adenosine phosphate-isopentenyltransferase enzyme 7, IPT7 or an adenosine phosphate-isopentenyltransferase enzyme 5, IPT5; and wherein said second nucleic acid sequence comprises a cambial specific promoter comprising a sequence having at least 95% sequence identity to SEQ ID NO:8.

14. The genetic construct according to claim 13, wherein said promoter comprises a *Populus* cambial specific promoter pLM5.

15. The genetic construct according to claim 14, wherein said *Populus* cambial specific promoter pLM5 has a sequence as set forth SEQ ID NO:8.

16. The genetic construct of claim 10, wherein said first nucleic acid has a sequence as set forth in SEQ ID NO:2.

17. A vector comprising or having contained therein a genetic construct according to claim 10.

* * * * *

SEQUENCE LISTING

```
<160> NUMBER OF SEQ ID NOS: 21

<210> SEQ ID NO 1
<211> LENGTH: 990
<212> TYPE: DNA
<213> ORGANISM: Arabidopsis thaliana

<400> SEQUENCE: 1
atgaagttct caatctcatc actgaagcag gtacaaccaa tcttgtgctt caagaacaag      60
ctatctaagg tcaacgtcaa ctctttctc catcccaaag aaaaagtcat ctttgtgatg     120
```

```
ggagctaccg gatcgggtaa gtctcgtctc gccatcgacc tagcaactcg tttcaagga    180 gagatcataa actccgacaa gattcaactt tacaagggcc tagacgtcct aacaaacaaa    240 gtcacccta  aagaatgccg aggcgtgcct caccacttgc ttggagtatt cgactccgaa    300
gccggaaacc taacggccac ccagtatagc cgccttgcgt cacaagcaat ctcgaaactc    360
tcagcgaaca acaagcttcc catagtagcc ggtggatcaa actcttacat cgaagcactt    420
gttaatcatt cctcggggtt tttattaaac aactacgatt gttgtttcat ttgggtcgac    480
gtttccttac ccgtacttaa ctcctttgtc tcaaaacgtg tcgaccgcat gatggaagca    540
ggattactcg aagaagtaag agaagtgttc aatccaaaag cgaattactc cgtagggata    600
cgacgagcta tcggagtccc cgagctccat gaatatttac gtaacgaatc tctagtggac    660
cgtgccacaa aaagtaaaat gcttgacgta gccgttaaaa atatcaaaaa gaacactgag    720
attttagctt gtcgacagtt aaaaaagatt caacggcttc acaagaagtg aagatgtct    780 atgcatcgtg ttgacgccac tgaggtgttc ttgaaacgca acgtagaaga acaagacgag    840
gcttgggaga atcttgtagc gagaccaagc gagagaatcg tcgataagtt ttataataat    900
aataaccaac tgaaaaatga tgatgttgag cactgtttgg cggcatctta cggcggagga    960
agtggaagta gagcccacaa tatgatatga                                     990
```

`<210>` SEQ ID NO 2  
`<211>` LENGTH: 329  
`<212>` TYPE: PRT  
`<213>` ORGANISM: Arabidopsis thaliana

`<400>` SEQUENCE: 2

```
Met Lys Phe Ser Ile Ser Ser Leu Lys Gln Val Gln Pro Ile Leu Cys
1               5                   10                  15

Phe Lys Asn Lys Leu Ser Lys Val Asn Val Asn Ser Phe Leu His Pro
            20                  25                  30

Lys Glu Lys Val Ile Phe Val Met Gly Ala Thr Gly Ser Gly Lys Ser
        35                  40                  45

Arg Leu Ala Ile Asp Leu Ala Thr Arg Phe Gln Gly Glu Ile Ile Asn
    50                  55                  60

Ser Asp Lys Ile Gln Leu Tyr Lys Gly Leu Asp Val Leu Thr Asn Lys
65                  70                  75                  80

Val Thr Pro Lys Glu Cys Arg Gly Val Pro His His Leu Leu Gly Val
                85                  90                  95

Phe Asp Ser Glu Ala Gly Asn Leu Thr Ala Thr Gln Tyr Ser Arg Leu
            100                 105                 110

Ala Ser Gln Ala Ile Ser Lys Leu Ser Ala Asn Asn Lys Leu Pro Ile
        115                 120                 125

Val Ala Gly Gly Ser Asn Ser Tyr Ile Glu Ala Leu Val Asn His Ser
    130                 135                 140

Ser Gly Phe Leu Leu Asn Asn Tyr Asp Cys Cys Phe Ile Trp Val Asp
145                 150                 155                 160

Val Ser Leu Pro Val Leu Asn Ser Phe Val Ser Lys Arg Val Asp Arg
                165                 170                 175

Met Met Glu Ala Gly Leu Leu Glu Glu Val Arg Glu Val Phe Asn Pro
            180                 185                 190

Lys Ala Asn Tyr Ser Val Gly Ile Arg Arg Ala Ile Gly Val Pro Glu
        195                 200                 205

Leu His Glu Tyr Leu Arg Asn Glu Ser Leu Val Asp Arg Ala Thr Lys
```

-continued

```
                210                 215                 220
Ser Lys Met Leu Asp Val Ala Val Lys Asn Ile Lys Asn Thr Glu
225                 230                 235                 240

Ile Leu Ala Cys Arg Gln Leu Lys Lys Ile Gln Arg Leu His Lys Lys
                245                 250                 255

Trp Lys Met Ser Met His Arg Val Asp Ala Thr Glu Val Phe Leu Lys
                260                 265                 270

Arg Asn Val Glu Glu Gln Asp Glu Ala Trp Glu Asn Leu Val Ala Arg
            275                 280                 285

Pro Ser Glu Arg Ile Val Asp Lys Phe Tyr Asn Asn Asn Gln Leu
        290                 295                 300

Lys Asn Asp Asp Val Glu His Cys Leu Ala Ala Ser Tyr Gly Gly Gly
305                 310                 315                 320

Ser Gly Ser Arg Ala His Asn Met Ile
                325
```

<210> SEQ ID NO 3
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: SITE
<222> LOCATION: (2)..(2)
<223> OTHER INFORMATION: Xaa = any amino acid
<220> FEATURE:
<221> NAME/KEY: SITE
<222> LOCATION: (4)..(5)
<223> OTHER INFORMATION: Xaa = any amino acid
<220> FEATURE:
<221> NAME/KEY: SITE
<222> LOCATION: (8)..(8)
<223> OTHER INFORMATION: Xaa = Ser or Thr

<400> SEQUENCE: 3

```
Gly Xaa Thr Xaa Xaa Gly Lys Xaa
1               5
```

<210> SEQ ID NO 4
<211> LENGTH: 16
<212> TYPE: PRT
<213> ORGANISM: Artificial
<220> FEATURE:
<223> OTHER INFORMATION: Consensus sequence
<220> FEATURE:
<221> NAME/KEY: SITE
<222> LOCATION: (1)..(1)
<223> OTHER INFORMATION: Xaa = Val or Leu or Ile
<220> FEATURE:
<221> NAME/KEY: SITE
<222> LOCATION: (2)..(8)
<223> OTHER INFORMATION: Xaa = any amino acid
<220> FEATURE:
<221> NAME/KEY: SITE
<222> LOCATION: (9)..(10)
<223> OTHER INFORMATION: Xaa = Val or Leu or Ile
<220> FEATURE:
<221> NAME/KEY: SITE
<222> LOCATION: (11)..(12)
<223> OTHER INFORMATION: Xaa = any amino acid
<220> FEATURE:
<221> NAME/KEY: SITE
<222> LOCATION: (14)..(15)
<223> OTHER INFORMATION: Xaa = any amino acid

<400> SEQUENCE: 4

```
Xaa Xaa Xaa Xaa Xaa Xaa Xaa Xaa Xaa Xaa Xaa Xaa Asp Xaa Xaa Gln
```

<210> SEQ ID NO 5
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: SITE
<222> LOCATION: (1)..(2)
<223> OTHER INFORMATION: Xaa = Val or Leu or Ile
<220> FEATURE:
<221> NAME/KEY: SITE
<222> LOCATION: (3)..(3)
<223> OTHER INFORMATION: Xaa can be any naturally occurring amino acid
<220> FEATURE:
<221> NAME/KEY: SITE
<222> LOCATION: (6)..(6)
<223> OTHER INFORMATION: Xaa = Ser or Thr

<400> SEQUENCE: 5

Xaa Xaa Xaa Gly Gly Xaa
1               5

<210> SEQ ID NO 6
<211> LENGTH: 102
<212> TYPE: PRT
<213> ORGANISM: Arabidopsis thaliana

<400> SEQUENCE: 6

Met Gly Ala Thr Gly Ser Gly Lys Ser Arg Leu Ala Ile Asp Leu Ala
1               5                   10                  15

Thr Arg Phe Gln Gly Glu Ile Ile Asn Ser Asp Lys Ile Gln Leu Tyr
                20                  25                  30

Lys Gly Leu Asp Val Leu Thr Asn Lys Val Thr Pro Lys Glu Cys Arg
            35                  40                  45

Gly Val Pro His His Leu Leu Gly Val Phe Asp Ser Glu Ala Gly Asn
        50                  55                  60

Leu Thr Ala Thr Gln Tyr Ser Arg Leu Ala Ser Gln Ala Ile Ser Lys
65                  70                  75                  80

Leu Ser Ala Asn Asn Lys Leu Pro Ile Val Ala Gly Gly Ser Asn Ser
                85                  90                  95

Tyr Ile Glu Ala Leu Val
            100

<210> SEQ ID NO 7
<211> LENGTH: 4720
<212> TYPE: DNA
<213> ORGANISM: Betula pendula

<400> SEQUENCE: 7
gagctcgtgt aacgtctaac attttaagt gaaaagtaac ttattgccta tcctttccac      60
tatgccatga ggctcgtgat tctatttatg catttgaatt ggttaattga tgataccagt    120
tgagaagttt tatctaaagt ttttattaat gtgagtcata gtcgtttgtt tttacgtaaa    180
atgattttcg ttaaaaatta gtttcaagaa atttgatttt caaaaaaata attttcgtcg    240
aaaacatttt tcggtatttg acatgtacga aaaatcgcaa atatttttt atattttcaa    300 ctaatcatat taacctataa aaattctttt tttatgcaca attaaaaaaa aaaaagttaa    360
atataaattg tcaagggcag gtctcggaga tgtcatgggc cggtcctgaa tgggtccgaa    420
tagtcccagc caggtcctag tggtgtctcg ggcgggtccc agtgatgttc tggtcagatt    480

```
ccggcgatgt tcgagcgga tctcgaaaat gttctaagtg agtccccgcg atgtcccgac    540
cgggtccccg tgacgtcatg ggcgggtccc gacaatgttt cgggcaagtc cgaaaaatgt    600
cctcagtggg tttcagcgat gtccttggtg ggtctcggca atgtcccaac tgggttccgg    660
tgacgtcctg gatgggttcg acgatgtccc aggtgggtcc cgaaataggt gggtcgcaac    720
gatgtctcga ggcgggtccc aaaaaatttc ttaagcgggt cccagcgatt ttccggccag    780
gtcccagcga tgtcccggca atgtcttgag tgggtcttgg cgatgtctta ggtaaatccc    840
ggcgatgtct cgactgggtt tcgaaaatat tttgggcgag tcctggcgat gtcctaagcg    900
ggtcctagca atgtcccggt cgggtctcga gaatatctcg agcgagtccc gactgggtcc    960
cggcaatttt ccgaataggt catgacgatg tttcaggcgg tcttgacag tgttttaatt     1020 gggtctgggc gatatcccaa gcggttcatg ttgatgttcc gggtaagtcc caaccgaatt    1080
ccggcagaat cttatagtgt tttgactatg gtccatcaat ttgagaatgt gacacttaaa    1140
cttaaaaaat gatttatggt tttaaaaata agaaactatt ttatgaaaat taagaaaat    1200 ttttggaca aactaaaaat ggtttcgttg actaatattt gtagtcccac taaatactga    1260
aaaatacaaa aaattatttt aaaaaattat tttatgccaa aacaaacgga gtcataaatt    1320
ccacaagatt tgaacttaaa atgtcactca ctacaacgtc aatgtgaaga cgtaatatca    1380
ttaaattatc atatttaat agaaaataaa tgtattttgt tcttaatcaa atgctgtttt    1440
aatcaattga attgtcaatt atctgagaca aacagacagt gcacgttgca acatagacga    1500
aagggcgttg ataatacaga aacaagatta aatttgggga gggtgaatag tcataataat    1560
aataatggaa aaatgtaaga ttagtttatg taattattcg gatttatgat aagtttttg    1620 tggcataaaa gttgctgaga ctttactgca gtatgcaaaa atagcaaatc gttcatgcat    1680
caaactttcg ttcaaatttt taatgaaaat tgttaaatgt tactaattaa attatgatac    1740
gtgtcactta taacaaaaaa tatataaaat ataaaactat aaatatataa aaaaaatta    1800 aagactaaaa attaaaaata aaaataaaaa gttgaaagag gaggtggcac agccacccag    1860
tttgagcata cctatgggtg gccgaaccat caccctatag tcattgaggg ccatttgagt    1920
gtggttaaac caccctcaat agctatggag tgatttgacc atctcccaga tatgaggtga    1980
tggttattgg ttaaccccaa atggccaaaa aaaaaaaaaa aaaaaaaagt tgattgatag    2040
tttggcgagc cttagatatg gttagagaga tggctgagcc atccttcttc tagttttttt    2100 ttttttttt ttttttttt ttacaaaaaa ttattttta attttaatt tttaacttt     2160 atatatttat ggtttcctat tttctatgtt tatatatata tttttattac aggtgacata    2220
tgtcataatt taattggagc tgatataaca ttttacgatt tctattgaaa ttttggacaa    2280
aaattagatg cataaaccta tttattattt gcataccaca gtgaggtcac aataaatttt    2340
tataccatta agagattatt ggaaatagat gtaacaaatg gactaatttt gcatttttt    2400 ttaataataa taaagaaca aaaagtcttc ttaattaatt aattactcat agcatagttg    2460
aataattctg tgagggtatt ttaggattcg ggtgaggaaa acaggggtta agaggtaaat    2520
aaggttggaa taagatctag gtcttgtcgc cgtgtcattg tcgccaagat ttgcgattgc    2580
gatctcaacc ctcccccacc ttcttattac caatcccatt ccaaacgccc ctcccctctc    2640
tctctctctc tcttaagctg agagagcaca tataaagaac aaagagctac aatttttttt    2700
ttttaaaaaa aagaacaaag aatcccagaa gagagcaaga aaggaaaaaa aaaaaatagg    2760
ctcttggttt tcccaaaata ggcttttggt ttcacttatt ttttaaattt ttttttggcc    2820
```

```
aactcttggt tgtttataa gctaaataaa taggagtaat actatttaat atagtattat    2880
agaacttgat gatgtaagag catatagcaa tgatatctat tttaactatt taaaatatga    2940
tgttttatct attttattta ttcactttt actataaatt ataacacata atttatttta    3000
ctatttattt tcaaaaaata ttattttta atcattttct tattattttt ttctgcttct    3060
ttgtctcact cttgctcaac attcttccat ctactaattt ttctcctttc tcttggcaaa    3120
gaacaaggac acatatatat atatatatat aagaaatcat tctcatagta ttttttatt    3180 tattattatt ttttattt tcttaaaaaa aataagtaaa tataaatgtg gcatatacac    3240
aataatgcaa tgagaatact gagtaatata tagatatata gtattcagcg catttttta    3300 ttattctctt tatttttta ttttcgttta aaaaaaaaca aaaggatgta aatgtgcaac    3360
ttgaaaaatg tgaacagcat ttatctttcc ttttactatt cagacccatt tgactaatag    3420
cacaaaggaa gtctgaccca cttgaagccc caaaacacg agagtggttc aattatagga    3480
ctcaatggtt ttggggtcac aaaattgcag agagagagag agagagaggg agaggagaca    3540
gagtgtgttg tgaaatagta gattattata agaagaagc cagagggaca gagagaggac    3600
tttaaagaga gagagagaga ggggacgagc agacaagagc gtatcttgga aaatcctaaa    3660
aattcgattt agtttttct ctttgttact ttaaaagca taggacaaac taaataaacc    3720
cccccatgaa ataaatctaa ctatttaaag aaaaaaaaa aacaagaaaa tagaactctt    3780 ttcccttgt tgttcattc attgtaccac accacaccct ccttcctctg cctagctact    3840
agctctacag gtaaaaaaca ttattattgt ttctttcaac aacccaccct ctgtctctct    3900
ctctctctga tattgctca cattctctct ctctgtttct gggttgtttg cgcttcgctg    3960
tttgttttgt gtgtctgtgt ctgtgttttt ttggggggtca atctgaggca tttgattgaa    4020
tattctaagg aagaaaagca gtgaacgtgc tcttctttt ccggacgcct ctactaaaaa    4080
acttcacgct ttttattag agtttggaga gaacaattat taagcgagtt tacactctgt    4140
atttttctat tcccatttct ttttaatca ttcaaagcct tgagacagac aggaacagac    4200 cccttgaca gagagactgt gatagaggct attctttgga atttgagctt ttttttctc    4260 ccccatcttt tgagagccat gcttgtctct cagaactgag tacttctctt tttaaaattc    4320
tgggtctctc tctgacctct cttctagat tctagcctac gaaatggctc tccagtgagt    4380
gagagggaga gagaatttg ttcaattgtt cgatattgct ttgttttgt tgtgggtgta    4440 cttatgccct ttgggaggt ttaaatcacg caaaacaatg ctctgtaatg ctaaatttac    4500
ttggagttct tgggtaccct ttttctttg atgccagaaa aagtgtgtc tgaaaagatt    4560 gccagtaatt tatcaaaagt tggcttatat atgtgtatgc attacttggg ggcctttta    4620 gcttaagata tgaagtgggt agtagcgagc aaacaagaag gtggagaaga aaagaaaac    4680 cagcaagaag agtcagagag aatttagtca gtgcttgctg    4720

<210> SEQ ID NO 8
<211> LENGTH: 1835
<212> TYPE: DNA
<213> ORGANISM: Populus tremula x Populus tremuloides

<400> SEQUENCE: 8
tcgtcttcaa gaattccaag cttggccaag cttctagaga tctgatgcaa aagctggaat      60
gagaatgcgc taaatgcgaa aagacagaga gagcgaataa atcgtgcaaa aaaggagtg     120 gggtgggtaa cgggttgagc tagaagaaga aaagggacag tgcactttta ggagggggc     180 aaccagagcg tagatgataa tggttcatgt ggaaacaaca cacatgagca gttggtgaga    240
```

```
acttgaatga acctaacag cccaaccaaa cccggagcca cccttaccga accaccactt      300
ctaaaagtac accatgcctt tttcttgagc ttggttgcac agggtgccag gtggggttgt      360
ttcgttttgg gtaatcatgc gatagtttaa ataacctttgc gataatcata tcaatggtga    420
cttttaagca catgttaggt gctcggttct tatctaaaca tggacatggc aacaagagtt     480
aatgctaaaa taatatacgt acattacctg tgaatgaatc gtcgctgtct tctgattatg     540
gcttcaaata atatgcagat aaacaagtgt cgatttttca gtgaagattt tatgaaagtg     600
cccgttctcc ttaagattac ctgtgaatga atcatccctg tcaggctgat cctgggtggt      660
ttttccccat gatgttcgga agatataatt atataaatga tggaatttac atgaaataag     720
tttcagtaca ttcttagcag aaaagcaata tcgacgaaga caaatgatgc tgtttaagac     780 aaactgggggt aatatcaatt tactagtaag agatttgtct gcttttctta attctcaaga   840
aactttcact aaaatgcaca gccatgttaa acaatttaca ttcaacttaa aaactaaaat    900
tgtaggatgg gtagctatcc aagaattacg cttttttgtaa acttaatttt gatgggcatg   960
tagttaacaa gtattttttca tcgatcaatt caagagccat gtctgcatca taattgtggg   1020
agtggagggg gcttttgttg ctagggaagg aatgccttct tagttcatgg ctttggactt    1080
cggacaagga gcgcatagaa tggggttacc attttttggaa aaattacatt tgaaccctcc  1140
aactattatc atatatgttt aatctacaat cctcgtccgc tagaagaagt ttgggttcaa     1200
agtaagcctt ttcatcggct caatgtaaac catggaggga ctaattgaaa aatagtatgt   1260
tagttggagg gtctgaatgt attatgtcca aacattctct tattattcct gtatcatctc    1320
tgagaaattc atccgaaaat aataaaacaa aatggccttt tttaaaataa gaagctgatg   1380
cataggatac caaaagcgcc ttgtccatta ggagcgtcag actttgaaaa taagaccaag  1440
aattccctgt aagctatcat ctcatctttt tttttgtttg aacttgtaga cgtaggcttt     1500
aagcgttcca tgatgttcag tcacatgttg ctgtctactt gattatgaa tttaattcat     1560 tcggctcata agaagataaa aggattatga cgttgaagaa ctctggtcac tccttagtta   1620
cggtcacata aaaacgatgc atctttcccc accaaccatc ttcaagtgaa cccacttttcc   1680 cttgcattag gtaaggagta tgggttaagt catcttcatg aaattagtcc cctagtggag   1740
ctaattctac tcactccata tttactcatt ccactatata acgccctcaa cgaccatcct    1800
caaagcaacc caaacacctt cttctcgtcg actct                                1835
```

<210> SEQ ID NO 9  
<211> LENGTH: 35  
<212> TYPE: DNA  
<213> ORGANISM: Artificial Sequence  
<220> FEATURE:  
<223> OTHER INFORMATION: IPT7_Fwd GW primer

<400> SEQUENCE: 9
acaaaaaagc aggcttaatg aagttctcaa tctca      35

<210> SEQ ID NO 10  
<211> LENGTH: 34  
<212> TYPE: DNA  
<213> ORGANISM: Artificial  
<220> FEATURE:  
<223> OTHER INFORMATION: IPT7_REV GW

<400> SEQUENCE: 10
tacaagaaag ctgggtatca tatcatattg tggg      34

<210> SEQ ID NO 11
<211> LENGTH: 11129
<212> TYPE: DNA
<213> ORGANISM: Artificial Sequence
<220> FEATURE:
<223> OTHER INFORMATION: fusion construct

<400> SEQUENCE: 11

```
cggcaggata tattcaattg taaatggctt catgtccggg aaatctacat ggatcagcaa        60
tgagtatgat ggtcaatatg gagaaaaaga aagagtaatt accaattttt tttcaattca       120
aaaatgtaga tgtccgcagc gttattataa aatgaaagta cattttgata aaacgacaaa       180
ttacgatccg tcgtatttat aggcgaaagc aataaacaaa ttattctaat tcggaaatct       240
ttatttcgac gtgtctacat tcacgtccaa atgggggctt agatgagaaa cttcacgatc       300
ggatctgcat cgcaggatgc tgctggctac cctgtggaac acctacatct gtattaacga       360
agcgctggca ttgaccctga gtgattttc tctggtcccg ccgcatccat accgccagtt       420
gtttaccctc acaacgttcc agtaaccggg catgttcatc atcagtaacc cgtatcgtga       480
gcatcctctc tcgtttcatc ggtatcatta cccccatgaa cagaaatccc ccttacacgg       540
aggcatcagt gaccaaacag gaaaaaaccg cccttaacat ggcccgcttt atcagaagcc       600
agacattaac gcttctggag aaactcaacg agctggacgc ggatgaacag gcagacatct       660
gtgaatcgct tcacgaccac gctgatgagc tttaccgcag ctgcctcgcg cgtttcggtg       720
atgacggtga aaacctctga cacatgcagc tcccggagac ggtcacagct tgtctgtaag       780
cggatgccgg gagcagacaa gcccgtcagg gcgcgtcagc gggtgttggc gggtgtcggg       840
gcgcagccat gacccagtca cgtagcgata gcggagtgta tactggctta actatgcggc       900
atcagagcag attgtactga gagtgcacca tatgcggtgt gaaataccgc acagatgcgt       960
aaggagaaaa taccgcatca ggcgctcttc cgcttcctcg ctcactgact cgctgcgctc      1020
ggtcgttcgg ctgcggcgag cggtatcagc tcactcaaag gcggtaatac ggttatccac      1080
agaatcaggg gataacgcag gaaagaacat gtgagcaaaa ggccagcaaa aggccaggaa      1140
ccgtaaaaag gccgcgttgc tggcgttttt ccataggctc cgcccccctg acgagcatca      1200
caaaaatcga cgctcaagtc agaggtggcg aaacccgaca ggactataaa gataccaggc      1260
gtttccccct ggaagctccc tcgtgcgctc tcctgttccg accctgccgc ttaccggata      1320
cctgtccgcc tttctccctt cgggaagcgt ggcgctttct catagctcac gctgtaggta      1380
tctcagttcg gtgtaggtcg ttcgctccaa gctgggctgt gtgcacgaac cccccgttca      1440
gcccgaccgc tgcgccttat ccggtaacta tcgtcttgag tccaacccgg taagacacga      1500
cttatcgcca ctggcagcag ccactggtaa caggattagc agagcgaggt atgtaggcgg      1560
tgctacagag ttcttgaagt ggtggcctaa ctacggctac actagaagga cagtatttgg      1620
tatctgcgct ctgctgaagc cagttaccct cggaaaaaga gttggtagct cttgatccgg      1680
caaacaaacc accgctggta gcggtggttt ttttgtttgc aagcagcaga ttacgcgcag      1740
aaaaaaagga tctcaagaag atcctttgat cttttctacg gggtctgacg ctcagtggaa      1800
cgaaaactca cgttaaggga ttttggtcat gagattatca aaaaggatct tcacctagat      1860
ccttttaaat taaaaatgaa gttttaaatc aatctaaagt atatatgagt aaacttggtc      1920
tgacagttac caatgcttaa tcagtgaggc acctatctca gcgatctgtc tatttcgttc      1980
atccatagtt gcctgactcc ccgtcgtgta gataactacg atacgggagg cttaccatc       2040
tggccccagt gctgcaatga taccgcgaga cccacgctca ccggctccag atttatcagc      2100
```

```
aataaaccag ccagccggaa gggccgagcg cagaagtggt cctgcaactt tatccgcctc    2160
catccagtct attaattgtt gccgggaagc tagagtaagt agttcgccag ttaatagttt    2220
gcgcaacgtt gttgccattg ctgcaggcat cgtggtgtca cgctcgtcgt ttggtatggc    2280
ttcattcagc tccggttccc aacgatcaag gcgagttaca tgatccccca tgttgtgcaa    2340
aaaagcggtt agctccttcg gtcctccgat cgttgtcaga agtaagttgg ccgcagtgtt    2400
atcactcatg gttatggcag cactgcataa ttctcttact gtcatgccat ccgtaagatg    2460
cttttctgtg actggtgagt actcaaccaa gtcattctga aatagtgta tgcggcgacc      2520 gagttgctct tgcccggcgt caacacggga taataccgcg ccacatagca gaactttaaa    2580
agtgctcatc attggaaaac gttcttcggg gcgaaaactc tcaaggatct taccgctgtt    2640
gagatccagt tcgatgtaac ccactcgtgc acccaactga tcttcagcat cttttacttt    2700
caccagcgtt tctgggtgag caaaaacagg aaggcaaaat gccgcaaaaa agggaataag    2760
ggcgacacgg aaatgttgaa tactcatact cttcctttt caatattatt gaagcattta     2820
tcagggttat tgtctcatga gcggatacat atttgaatgt atttagaaaa ataaacaaat    2880
aggggttccg cgcacatttc cccgaaaagt gccacctgac gtctaagaaa ccattattat    2940
catgacatta acctataaaa ataggcgtat cacgaggccc tttcgtcttc aagaattcca    3000
agcttggcca agcttctaga gatctgatgc aaaagctgga atgagaatgc gctaaatgcg    3060
aaaagacaga gagagcgaat aaatcgtgca aaaaaggag tggggtgggt aacgggttga     3120
gctagaagaa gaaaagggac aagtgcactt taggaggggg gcaaccagag cgtagatgat    3180
aatggttcat gtggaaacaa cacacatgag cagttggtga aacttgaat gaaccctaac     3240 agcccaacca aacccggagc caccttacc gaaccaccac ttctaaaagt acaccatgcc      3300
tttttcttga gcttggttgc acagggtgcc aggtggggtt gtttcgtttt gggtaatcat    3360
gcgatagttt aaataccttt gcgataatca tatcaatggt gactttaag cacatgttag      3420 gtgctcggtt cttatctaaa catggacatg gcaacaagag ttaatgctaa aataatatac    3480
gtacattacc tgtgaatgaa tcgtcgctgt cttctgatta tggcttcaaa taatatgcag    3540
ataaacaagt gtcgattttt cagtgaagat tttatgaaag tgcccgttct ccttaagatt    3600
acctgtgaat gaatcatccc tgtcaggctg atcctgggtg gttttcccc atgatgttcg     3660 gaagatataa ttatataaat gatggaattt acatgaaata gtttcagta cattcttagc     3720 agaaaagcaa tatcgacgaa gacaaatgat gctgtttaag acaaactggg gtaatatcaa    3780
tttactagta agagatttgt ctgcttttct taattctcaa gaaactttca ctaaaatgca    3840
cagccatgtt aaacaattta cattcaactt aaaaactaaa attgtaggat gggtagctat    3900
ccaagaatta cgcttttgt aaacttaatt ttgatggca tgtagttaac aagtattttt       3960
catcgatcaa ttcaagagcc atgtctgcat cataattgtg ggagtggagg gggcttttgt    4020
tgctagggaa ggaatgcctt cttagttcat ggctttggac ttcggacaag gagcgcatag    4080 aatgggggtta ccattttgg aaaaattaca tttgaaccct ccaactatta tcatatatgt    4140
ttaatctaca atcctcgtcc gctagaagaa gtttgggttc aaagtaagcc ttttcatcgg    4200
ctcaatgtaa accatggagg gactaattga aaaatagtat gttagttgga gggtctgaat    4260
gtattatgtc caaacattct cttattattc ctgtatcatc tctgagaaat tcatccgaaa    4320
ataataaaac aaaatggcct ttttaaaat aagaagctga tgcataggat accaaaagcg     4380
ccttgtccat taggagcgtc agactttgaa aataagacca agaattccct gtaagctatc    4440
```

```
atctcatctt ttttttttgtt tgaacttgta gacgtaggct ttaagcgttc catgatgttc    4500
agtcacatgt tgctgtctac ttgattatgg aatttaattc attcggctca taagaagata    4560
aaaggattat gacgttgaag aactctggtc actccttagt tacggtcaca taaaaacgat    4620
gcatctttcc ccaccaacca tcttcaagtg aacccacttt cccttgcatt aggtaaggag    4680
tatgggttaa gtcatcttca tgaaattagt ccccctagtgg agctaattct actcactcca    4740
tatttactca ttccactata taacgccctc aacgaccatc ctcaaagcaa cccaaacacc    4800
ttcttctcgt cgactctaga ggatcaatca acaagtttgt acaaaaaagc aggcttaatg    4860
aagttctcaa tctcatcact gaagcaggta caaccaatct tgtgcttcaa gaacaagcta    4920
tctaaggtca acgtcaactc ttttctccat cccaaagaaa aagtcatctt tgtgatggga    4980
gctaccggat cggtaagtc tcgtctcgcc atcgacctag caactcgttt tcaaggagag    5040
atcataaact ccgacaagat tcaactttac aagggcctag acgtcctaac aaacaaagtc    5100 accccctaaag aatgccgagg cgtgcctcac cacttgcttg gagtattcga ctccgaagcc    5160
ggaaacctaa cggccaccca gtatagccgc cttgcgtcac aagcaatctc gaaactctca    5220
gcgaacaaca agcttcccat agtagccggt ggatcaaact cttacatcga agcacttgtt    5280
aatcattcct cggggttttt attaaacaac tacgattgtt gtttcatttg ggtcgacgtt    5340
tccttacccg tacttaactc ctttgtctca aaacgtgtcg accgcatgat ggaagcagga    5400
ttactcgaag aagtaagaga agtgttcaat ccaaaagcga attactccgt agggatacga    5460
cgagctatcg gagtccccga gctccatgaa tatttacgta acgaatctct agtggaccgt    5520
gccacaaaaa gtaaaatgct tgacgtagcc gttaaaaata tcaaaaagaa cactgagatt    5580
ttagcttgtc gacagttaaa aaagattcaa cggcttcaca agaagtggaa gatgtctatg    5640
catcgtgttg acgccactga ggtgttcttg aaacgcaacg tagaagaaca agacgaggct    5700
tgggagaatc ttgtagcgag accaagcgag agaatcgtcg ataagtttta taataataat    5760
aaccaactga aaaatgatga tgttgagcac tgtttggcgg catcttacgg cggaggaagt    5820
ggaagtagag cccacaatat gatatgatac ccagctttct tgtacaaagt ggttgatgag    5880
ctcgaatttc cccgatcgtt caaacatttg gcaataaagt ttcttaagat tgaatcctgt    5940
tgccggtctt gcgatgatta tcatataatt tctgttgaat tacgttaagc atgtaataat    6000
taacatgtaa tgcatgacgt tatttatgag atgggttttt atgattagag tcccgcaatt    6060
atacatttaa tacgcgatag aaaacaaaat atagcgcgca aactaggata aattatcgcg    6120
cgcggtgtca tctatgttac tagatcggga attgtaaccc ggatctctag ctagaagcta    6180
gcttcacgct gccgcaagca ctcagggcgc aagggctgct aaaggaagcg gaacacgtag    6240
aaagccagtc cgcagaaacg gtgctgaccc cggatgaatg tcagctactg gctatctgg    6300 acaagggaaa acgcaagcgc aaagagaaag caggtagctt gcagtgggct tacatggcga    6360
tagctagact gggcggtttt atggacagca agcgaaccgg aattgccagc tggggcgccc    6420
tctggtaagg ttgggaagcc ctgcaaagta aactggatgg ctttcttgcc gccaaggatc    6480
tgatggcgca ggggatcaag atcatgagcg gagaattaag ggagtcacgt tatgaccccc    6540
gccgatgacg cgggacaagc cgttttacgt ttggaactga cagaaccgca acgttgaagg    6600
agccactcag ccgcgggttt ctggagttta atgagctaag cacatacgtc agaaaccatt    6660
attgcgcgtt caaagtcgc ctaaggtcac tatcagctag caaatatttc ttgtcaaaaa    6720
tgctccactg acgttccata aattcccctc ggtatccaat tagagtctca tattcactct    6780
caatccagat cgggggcaa taagatatga aaaagcctga actcaccgcg acgtctgtcg    6840
```

```
agaagtttct gatcgaaaag ttcgacagcg tctccgacct gatgcagctc tcggagggcg    6900
aagaatctcg tgctttcagc ttcgatgtag gagggcgtgg atatgtcctg cgggtaaata    6960
gctgcgccga tggtttctac aaagatcgtt atgtttatcg cactttgca tcggccgcgc    7020 tcccgattcc ggaagtgctt gacattgggg cattcagcga gagcctgacc tattgcatct    7080
cccgccgtgc acagggtgtc acgttgcaag acctgcctga aaccgaactg cccgctgttc    7140
tgcagccggt cgcggaggcc atggatgcga tcgctgcggc cgatcttagc cagacgagcg    7200
ggttcggccc attcggaccg caaggaatcg gtcaatacac tacatggcgt gatttcatat    7260
gcgcgattgc tgatccccat gtgtatcact ggcaaactgt gatggacgac accgtcagtg    7320
cgtccgtcgc gcaggctctc gatgagctga tgctttgggc cgaggactgc cccgaagtcc    7380
ggcacctcgt gcacgcggat ttcggctcca acaatgtcct gacggacaat ggccgcataa    7440
cagcggtcat tgactggagc gaggcgatgt tcggggattc ccaatacgag gtcgccaaca    7500
tcttcttctg gaggccgtgg ttggcttgta tggagcagca gacgcgctac ttcgagcgga    7560
ggcatccgga gcttgcagga tcgccgcggc tccgggcgta tatgctccgc attggtcttg    7620
accaactcta tcagagcttg gttgacggca atttcgatga tgcagcttgg gcgcagggtc    7680
gatgcgacgc aatcgtccga tccggagccg ggactgtcgg gcgtacacaa atcgcccgca    7740
gaagcgcggc cgtctggacc gatggctgtg tagaagtact cgccgatagt ggaaaccgac    7800
gccccagcac tcgtccgagg gcaaaggaat agagtagatg ccgaccggga tcttcgatcc    7860
ccgatcgttc aaacatttgg caataaagtt tcttaagatt gaatcctgtt gccggtcttg    7920
cgatgattat catataattt ctgttgaatt acgttaagca tgtaataatt aacatgtaat    7980
gcatgacgtt atttatgaga tgggttttta tgattagagt cccgcaatta tacatttaat    8040
acgcgataga aaacaaaata tagcgcgcaa actaggataa attatcgcgc gcggtgtcat    8100
ctatgttact agatcgggaa ttgccaagct gatcagattg tcgtttcccg ccttcggttt    8160
aaactatcag tgtttgacag gatatattgg cgggtaaacc taagagaaaa gagcgtttat    8220
tagaataatc ggatatttaa aagggcgtga aaaggtttat ccgttcgtcc atttgtatgt    8280
gcatgccaac cacagggttc ccctcgggag tgcttggcat tccgtgcgat aatgacttct    8340
gttcaaccac ccaaacgtcg gaaagcctga cgacggagca gcattccaaa agatcccctt    8400
ggctcgtctg ggtcggctag aaggtcgagt gggctgctgt ggcttgatcc ctcaacgcgg    8460
tcgcggacgt agcgcagcgc cgaaaaatcc tcgatcgcaa atccgacgct gtcgaaaagc    8520
gtgatctgct tgtcgctctt tcggccgacg tcctggccag tcatcacgcg ccaaagttcc    8580
gtcacaggat gatctggcgc gagttgctgg atctcgcctt caatccgggt ctgtggcggg    8640
aactccacga aaatatccga acgcagcaag atatcgcggt gcatctcggt cttgcctggg    8700
cagtcgccgc cgacgccgtt gatgtggacg ccgtcgagat ccggattttg tagccctggc    8760
cgacggccag caggtaggcc gacaggctca tgccggccgc cgccgccttt tcctcaatcg    8820
ctcttcgttc gtctggaagg cagtacacct tgataggtgg gctgcccttc ctggttggct    8880
tggtttcatc agccatccgc ttgccctcat ctgttacgcc ggcggtagcc ggccagcctc    8940
gcagagcagg attcccgttg agcaccgcca ggtgcgaata agggacagtg aagaaggaac    9000
acccgctcgc gggtgggcct acttcaccta tcctgcccgg ctgacgccgt tggatacacc    9060
aaggaaagtc tacacgaacc cttttggcaaa atcctgtata tcgtgcgaaa aaggatggat    9120
ataccgaaaa aatcgctata atgaccccga agcagggtta tgcagcggaa aagcgctgct    9180
```

-continued

```
tccctgctgt tttgtggaat atctaccgac tggaaacagg caaatgcagg aaattactga    9240
actgagggga caggcgagag acgatgccaa agagctacac cgacgagctg gccgagtggg    9300
ttgaatcccg cgcggccaag aagcgccggc gtgatgaggc tgcggttgcg ttcctggcgg    9360
tgagggcgga tgtcgaggcg gcgttagcgt ccggctatgc gctcgtcacc atttgggagc    9420
acatgcggga aacggggaag gtcaagttct cctacgagac gttccgctcg cacgccaggc    9480
ggcacatcaa ggccaagccc gccgatgtgc ccgcaccgca ggccaaggct gcggaacccg    9540
cgccggcacc caagacgccg gagccacggc ggccgaagca gggggggcaag gctgaaaagc    9600 cggcccccgc tgcggccccg accggcttca ccttcaaccc aacaccggac aaaaaggatc    9660
tagcgtggac tcaaggctct cgcgaatggc tcgcgttgga aactttcatt gacacttgag    9720
gggcaccgca gggaaattct cgtccttgcg agaaccggct atgtcgtgct gcgcatcgag    9780
cctgcgccct tggcttgtct cgcccctctc cgcgtcgcta cggggcttcc agcgcctttc    9840
cgacgctcac cgggctggtt gcctcgccg ctgggctggc ggccgtctat ggccctgcaa     9900
acgcgccaga aacgccgtcg aagccgtgtg cgagacaccg cggccgccgg cgttgtggat    9960
acctcgcgga aaacttggcc ctcactgaca gatgagggc ggacgttgac acttgagggg    10020
ccgactcacc cggcgcggcg ttgacagatg aggggcaggc tcgatttcgg ccggcgacgt    10080
ggagctggcc agcctcgcaa atcggcgaaa acgcctgatt ttacgcgagt tcccacaga    10140 tgatgtggac aagcctgggg ataagtgccc tgccggtattg acacttgagg ggcgcgacta    10200
ctgacagatg aggggcgcga tccttgacac ttgagggca gagtgctgac agatgagggg    10260
cgcacctatt gacatttgag gggctgtcca caggcagaaa atccagcatt tgcaagggtt    10320
tccgcccgtt tttcggccac cgctaacctg tcttttaacc tgcttttaaa ccaatattta    10380
taaaccttgt ttttaaccag ggctgcgccc tgtgcgcgtg accgcgcacg ccgaaggggg    10440 gtgcccccccc ttctcgaacc ctcccggccc gctaacgcgg gcctccatc cccccagggg    10500 ctgcgcccct cggccgcgaa cggcctcacc ccaaaaatgg cagcgctggc agtccttgcc    10560
attgccggga tcggggcagt aacgggatgg gcgatcagcc cgagcgcgac gcccggaagc    10620
attgacgtgc cgcaggtgct ggcatcgaca ttcagcgacc aggtgccggg cagtgagggc    10680
ggcggcctgg gtggcggcct gcccttcact tcggccgtcg gggcattcac ggacttcatg    10740
gcggggccgc caattttttac cttgggcatt cttggcatag tggtcgcggg tgccgtgctc    10800
gtgttcgggg gtgaattgca agctagcttg cttggtcgtt ccggtaccgt gaacgtcggc    10860
tcgattgtac ctgcgttcaa atactttgcg atcgtgttgc gcgcctgccc ggtgcgtcgg    10920
ctgatctcac ggatcgactg cttctctcgc aacgccatcc gacggatgat gtttaaaagt    10980
cccatgtgga tcactccgtt gccccgtcgc tcaccgtgtt gggggaagg tgcacatggc    11040 tcagttctca atggaaatta tctgcctaac cggctcagtt ctgcgtagaa accaacatgc    11100
aagctccacc gggtgcaaag cggcagcgg                                     11129
```

<210> SEQ ID NO 12
<211> LENGTH: 101
<212> TYPE: PRT
<213> ORGANISM: Populus trichocarpa

<400> SEQUENCE: 12

Met Gly Thr Thr Ala Thr Gly Lys Ser Lys Leu Ser Ile Asp Leu Ala
1               5                   10                  15

Thr His Phe Gln Gly Glu Ile Ile Asn Ser Asp Lys Ile Gln Val Tyr
            20                  25                  30

Lys Gly Leu Asp Met Leu Thr Asn Lys Ile Ser Glu Ile Glu Arg Arg
        35                  40                  45

Gly Val Pro His His Leu Leu Gly Phe Val Glu Pro Gly Glu Glu Phe
    50                  55                  60

Thr Thr Gln Asp Phe Cys Asn His Val His Lys Ala Met Lys His Ile
65                  70                  75                  80

Thr Gly Asp Gly Ser Ile Pro Ile Ile Ala Gly Gly Ser Asn Arg Tyr
                85                  90                  95

Ile Glu Ala Leu Val
            100

<210> SEQ ID NO 13
<211> LENGTH: 101
<212> TYPE: PRT
<213> ORGANISM: Populus trichocarpa

<400> SEQUENCE: 13

Met Gly Thr Thr Ala Thr Gly Lys Ser Lys Leu Ser Ile Asp Leu Ala
1               5                   10                  15

Thr His Phe Gln Gly Glu Ile Ile Asn Ser Asp Lys Ile Gln Val Tyr
            20                  25                  30

Lys Gly Leu Asp Ile Leu Thr Asn Lys Val Ser Glu Asp Glu Ser Arg
        35                  40                  45

Gly Val Pro His His Leu Leu Gly Phe Val Glu Pro Gly Glu Glu Phe
    50                  55                  60

Thr Thr Gln Asp Phe Cys Asn His Val His Met Ala Met Arg His Ile
65                  70                  75                  80

Ile Gly Asn Gly Asn Ile Pro Ile Ile Ala Gly Gly Ser Asn Arg Tyr
                85                  90                  95

Ile Glu Ala Leu Val
            100

<210> SEQ ID NO 14
<211> LENGTH: 102
<212> TYPE: PRT
<213> ORGANISM: Arabidopsis thaliana

<400> SEQUENCE: 14

Met Gly Ala Thr Gly Ser Gly Lys Ser Arg Leu Ala Ile Asp Leu Ala
1               5                   10                  15

Thr Arg Phe Gln Gly Glu Ile Ile Asn Ser Asp Lys Ile Gln Leu Tyr
            20                  25                  30

Lys Gly Leu Asp Val Leu Thr Asn Lys Val Thr Pro Lys Glu Cys Arg
        35                  40                  45

Gly Val Pro His His Leu Leu Gly Val Phe Asp Ser Glu Ala Gly Asn
    50                  55                  60

Leu Thr Ala Thr Gln Tyr Ser Arg Leu Ala Ser Gln Ala Ile Ser Lys
65                  70                  75                  80

Leu Ser Ala Asn Asn Lys Leu Pro Ile Val Ala Gly Gly Ser Asn Ser
                85                  90                  95

Tyr Ile Glu Ala Leu Val
            100

<210> SEQ ID NO 15
<211> LENGTH: 102
<212> TYPE: PRT
<213> ORGANISM: Eucalyptus grandis

<400> SEQUENCE: 15

Met Gly Ala Thr Gly Thr Gly Lys Ser Lys Leu Ser Ile Asn Leu Ala
1               5                   10                  15

Val His Tyr Gln Thr Glu Val Ile Asn Ser Asp Lys Ile Gln Val Tyr
            20                  25                  30

Lys Gly Leu Asp Val Val Thr Asn Lys Val Thr Asp Leu Glu Cys Arg
        35                  40                  45

Gly Val Pro His His Leu Leu Gly Val Ile Asp Pro Asp Val Asp
    50                  55                  60

Phe Ser Val His Asp Phe Cys Arg Asp Ala Leu Thr Ala Ile Asn Gln
65                  70                  75                  80

Ile Thr Gln Arg Gly Arg Ala Ala Ile Val Ala Gly Gly Ser Asn Ser
            85                  90                  95

Phe Ile Glu Val Leu Val
            100

<210> SEQ ID NO 16
<211> LENGTH: 102
<212> TYPE: PRT
<213> ORGANISM: Eucalyptus grandis

<400> SEQUENCE: 16

Met Gly Ala Thr Gly Thr Gly Lys Ser Lys Leu Ser Ile Asn Leu Ala
1               5                   10                  15

Val His Tyr Gln Thr Glu Val Ile Asn Ser Asp Lys Ile Gln Val Tyr
            20                  25                  30

Lys Gly Leu Asp Val Val Thr Asn Lys Val Thr Asp Leu Glu Cys Arg
        35                  40                  45

Gly Val Pro His His Leu Leu Gly Val Ile Asp Pro Asp Val Asp
    50                  55                  60

Phe Ser Val His Asp Phe Cys Arg Asp Ala Leu Thr Ala Ile Asn Gln
65                  70                  75                  80

Ile Thr Gln Arg Gly Arg Ala Ala Ile Val Ala Gly Gly Ser Asn Ser
            85                  90                  95

Phe Ile Glu Val Leu Val
            100

<210> SEQ ID NO 17
<211> LENGTH: 102
<212> TYPE: PRT
<213> ORGANISM: Arabidopsis thaliana

<400> SEQUENCE: 17

Met Gly Ala Thr Gly Thr Gly Lys Ser Arg Leu Ala Ile Asp Leu Ala
1               5                   10                  15

Thr Arg Phe Pro Ala Glu Ile Val Asn Ser Asp Lys Ile Gln Val Tyr
            20                  25                  30

Lys Gly Leu Asp Ile Val Thr Asn Lys Val Thr Pro Glu Glu Ser Leu
        35                  40                  45

Gly Val Pro His His Leu Leu Gly Thr Val His Asp Thr Tyr Glu Asp
    50                  55                  60

Phe Thr Ala Glu Asp Phe Gln Arg Glu Ala Ile Arg Ala Val Glu Ser
65                  70                  75                  80

Ile Val Gln Arg Asp Arg Val Pro Ile Ile Ala Gly Gly Ser Asn Ser
            85                  90                  95

Tyr Ile Glu Ala Leu Val
            100

<210> SEQ ID NO 18
<211> LENGTH: 101
<212> TYPE: PRT
<213> ORGANISM: Populus trichocarpa

<400> SEQUENCE: 18

Leu Gly Pro Thr Gly Thr Gly Lys Ser Arg Leu Ala Ile Asp Leu Ala
1               5                   10                  15

Thr His Phe Pro Ala Glu Val Val Asn Cys Asp Lys Met Gln Val Tyr
            20                  25                  30

Lys Gly Leu Asp Ile Val Thr Asn Lys Val Thr Glu Glu Cys Arg
        35                  40                  45

Gly Val Pro His His Leu Leu Gly Ile Ala Asp Pro Asn Ala Asp Phe
    50                  55                  60

Thr Ser Asp Asp Phe Arg His His Ala Ser Leu Val Val Glu Ser Ile
65                  70                  75                  80

Val Thr Arg Asp Arg Leu Pro Ile Ile Ala Gly Gly Ser Asn Ser Tyr
                85                  90                  95

Val Glu Ala Leu Ala
            100

<210> SEQ ID NO 19
<211> LENGTH: 101
<212> TYPE: PRT
<213> ORGANISM: Populus trichocarpa

<400> SEQUENCE: 19

Val Gly Pro Thr Gly Thr Gly Lys Ser Arg Leu Ala Ile Asp Leu Ala
1               5                   10                  15

Thr Arg Phe Pro Ala Glu Val Val Asn Cys Asp Lys Met Gln Val Tyr
            20                  25                  30

Lys Gly Leu Asp Ile Val Thr Asn Lys Val Thr Glu Glu Cys Arg
        35                  40                  45

Gly Val Pro His His Leu Leu Gly Ile Ala Asp Pro Asn Ala Asn Phe
    50                  55                  60

Thr Ser Asp Asp Phe Arg His His Ala Ser Leu Val Val Glu Ser Ile
65                  70                  75                  80

Val Thr Arg Asp Arg Leu Pro Ile Ile Ala Gly Gly Ser Asn Ser Tyr
                85                  90                  95

Ile Glu Ala Leu Ala
            100

<210> SEQ ID NO 20
<211> LENGTH: 101
<212> TYPE: PRT
<213> ORGANISM: Eucalyptus grandis

<400> SEQUENCE: 20

Met Gly Ala Thr Gly Thr Gly Lys Ser Arg Leu Ala Ile Asp Leu Ala
1               5                   10                  15

Thr His Phe Pro Gly Glu Val Ile Asn Ser Asp Lys Met Gln Val Tyr
            20                  25                  30

Lys Gly Leu Asn Ile Val Thr Asn Lys Val Thr Lys Glu Glu Cys Arg
        35                  40                  45

Glu Ile Pro His His Leu Leu Gly Phe Val Asp Pro Asp Ser Asp Phe

-continued

```
                    50                  55                  60
Thr Ala Thr Asp Phe Arg Asp His Thr Ser Leu Ala Leu Pro Ser Ile
 65                  70                  75                  80

Ser Arg Gln Asp Arg Val Pro Ile Ile Ala Gly Gly Ser Asn Ser Phe
                 85                  90                  95

Ile Glu Ala Leu Val
            100

<210> SEQ ID NO 21
<211> LENGTH: 101
<212> TYPE: PRT
<213> ORGANISM: Eucalyptus grandis

<400> SEQUENCE: 21

Val Gly Ala Thr Gly Thr Gly Lys Ser Arg Leu Ala Ile Asp Leu Ala
 1               5                  10                  15

Asp Arg Phe Arg Gly Glu Val Val Asn Ser Asp Lys Ile Gln Val Tyr
                20                  25                  30

Lys Gly Leu Asp Ile Val Thr Asn Lys Val Thr Glu Glu Glu Cys Arg
             35                  40                  45

Gly Val Pro His His Leu Leu Gly Ile Ala Glu Pro Asp Ser Glu Phe
         50                  55                  60

Thr Ala Ile Asp Phe Arg Cys His Ala Leu Leu Ala Ile Asp Ser Ile
 65                  70                  75                  80

Leu Ala Arg Gly Arg Leu Pro Ile Ile Ala Gly Gly Ser Asn Ser Phe
                 85                  90                  95

Ile Asp Ala Leu Val
            100
```